United States Patent
Cervino et al.

(10) Patent No.: US 11,898,210 B2
(45) Date of Patent: Feb. 13, 2024

(54) TOOLS FOR ASSESSING FIMH BLOCKERS THERAPEUTIC EFFICIENCY

(71) Applicant: ENTEROME, Paris (FR)

(72) Inventors: Alessandra Cervino, Bois-le-Roi (FR);
Christophe Bonny, Paris (FR);
Jonathan Plassais, Asnieres-sur-Seine (FR)

(73) Assignee: ENTEROME, Paris (FR)

( * ) Notice: Subject to any disclaimer, the term of this patent is extended or adjusted under 35 U.S.C. 154(b) by 756 days.

(21) Appl. No.: 16/755,829

(22) PCT Filed: Oct. 16, 2018

(86) PCT No.: PCT/EP2018/078297
§ 371 (c)(1),
(2) Date: Apr. 13, 2020

(87) PCT Pub. No.: WO2019/076931
PCT Pub. Date: Apr. 25, 2019

(65) Prior Publication Data
US 2020/0277655 A1      Sep. 3, 2020

(30) Foreign Application Priority Data
Oct. 16, 2017   (EP) .................................... 17306402

(51) Int. Cl.
*C12Q 1/689*     (2018.01)
*A61K 31/7064*   (2006.01)

(52) U.S. Cl.
CPC .......... *C12Q 1/689* (2013.01); *A61K 31/7064* (2013.01); *C12Q 2600/106* (2013.01)

(58) Field of Classification Search
CPC ....................................................... C12Q 1/689
See application file for complete search history.

(56) References Cited

FOREIGN PATENT DOCUMENTS

WO        2006025702 A1     3/2006
WO     WO-2015110609 A1 *   7/2015  ............. A61K 31/70

OTHER PUBLICATIONS

Gurnee, E.A. et al., Gut Colonization of Healthy Children and Their Mothers With Pathogenic Ciprofloxacin-Resistant *Escherichia coli*, J. Infect. Dis., vol. 212, pp. 1862-1868 (Year: 2015).*
Schwan, W.R., Regulation of fim genes in uropathogenic *Escherichia coli*, World J. Clin. Infect. Dis., vol. 1, pp. 17-25 (Year: 2011).*
Sivignon, A. et al., The potential of FimH as a novel therapeutic target for the treatment of Crohn's disease, Expert Opinion on Therapeutic Targets, vol. 21, pp. 837-847 (Year: 2017).*
Mydock-McGrane, L.K. et al., Mannose-derived FimH antagonists: a promising anti-virulence therapeutic strategy for urinary tract infections and Crohn's disease, Expert Opinion on Therapeutic Patents, vol. 26, pp. 175-197 (Year: 2016).*

(Continued)

*Primary Examiner* — Teresa E Strzelecka
(74) *Attorney, Agent, or Firm* — Arrigo, Lee, Guttman & Mouta-Bellum LLP

(57) ABSTRACT

The present invention relates to an in vitro method for identifying subjects hosting high amounts of Fim H expressing proteobacteria in their gut, said method comprising the step of detecting the expression of the fimH gene in a stool sample of said subjects.

8 Claims, 10 Drawing Sheets

Specification includes a Sequence Listing.

ON

OFF

(56) References Cited

OTHER PUBLICATIONS

Flores-Mireles, A. L. et al., Urinary tract infections: epidemiology, mechanisms of infection and treatment options, Nature Reviews, vol. 13, pp. 269-284 (Year: 2015).*
Ayoib A. et al. DNA extraction on bio-chip: history and preeminence over conventional and solid-phase extraction methods. Appl Microbiol Biotechnol. 2017, 101, 8077-8088.
Barnich N et al., Regulatory and functional co-operation of flagella and type 1 pili in adhesive and invasive abilities of AIEC strain LF82 isolated from a patient with Crohn's disease. Mol. Microbiol. 2003, 48, 781-794.
Barnich N et al, CEACAM6 acts as a receptor for adherent-invasive *E. coli*, supporting ileal mucosa colonization in Crohn diseaseJ. Clin. Invest 2007, 117, 1566-1574.
Barnich N et al, Abnormal CEACAM6 expression in Crohn disease patients favors gut colonization and inflammation by adherent-invasive *E. coli*. Virulence Jul.-Aug. 2010, 1(4), 281-282.
Barnich N. et al, The Presence of Adherent-Invasive *Escherichia coli* (AIEC) on the Surgical Specimen is a Predictor of Severe Endoscopic Postoperative Recurrence in Ileal Crohn's Disease. AGA Abstract, 2017, S-9, p. 1.
Bennett et al, Induction of Colonic M Cells during Intestinal Inflammation. Am J of Pathology 2016, 186(5), 1166-1179.
Best WR et al, Development of a Crohn's Disease Activity Index National Cooperative Crohn's Disease Study, Gastroenterology 1976, 70(3), 439-444.
Baumgart M. et al., Culture independent analysis of ileal mucosa reveals a selective increase in invasive *Escherichia coli* of novel phylogeny relative to depletion of Clostridiales in Crohn's disease involving the ileum, ISME J., 2007, 1(5), 403-418.
Bouckaert J et al. Receptor Binding Studies Disclose a Novel Class of High-Affinity Inhibitors of the *Escherichia coli* FimH Adhesin. Mol. Microbiol. 2005, 55, 441-455.
Bouckaert J et al. The affinity of the FimH fimbrial adhesin is receptor-driven and quasi-independent of *Escherichia coli* pathotypes. Mol. Microbiol. 2006, 61(6), 1556-1568.
Bouckaert J et al. Heptyl a-d-Mannosides Grafted on a b-Cyclodextrin Core to Interfere with *Escherichia coli* Adhesion: An In Vivo Multivalent Effect Chemistry, a European Journal, 2013, 19, 7847-7855.
Boudeau J et al. Invasive Ability of an *Escherichia coli* Strain Isolated from the Ileal Mucosa of a Patient with Crohn's Disease Infect. Immun. 1999, 67, 4499-4509.
Boudeau J. et al, Type 1 pili-mediated adherence of *Escherichia coli* strain LF82 isolated from Crohn's disease is involved in bacterial invasion of intestinal epithelial cellsMol. Microbiol. 2001, 39(5), 1272-1284.
Bringer MA. et al, The Crohn's disease-associated adherent-invasive *Escherichia coli* strain LF82 replicates in mature phagolysosomes within J774 macrophages. Cellular Microbiology, 2006, 8(3), 471-484.
Brument et al. Thiazolylaminomannosides as Potent Antiadhesives of Type 1 Piliated *Escherichia coli* Isolated from Crohn's Disease Patients. Journal of Medicinal Chemistry 2013, 56(13), 5395-5406.
Burns L. et al., Interaction of the FimB Integrase with the fimS Invertible DNA Element in *Escherichia coli* In Vivo and In Vitro. Journal of Bacteriology, May 2000, 182(10) p. 2953-2959.
Chalopin T. et al, Inhibition profiles of mono- and polyvalent FimH antagonists against 10 different *Escherichia coli* strains. Org. Biomol. Chem., 2015, 13, 11369-11375.
Chassaing et al. Crohn disease-associated adherent-invasive *E. coli* bacteria target mouse and human Peyer's patches via long polar fimbriae. J Clin Invest. 2011, 121(3), 966-975.
Cho et al. Recent Insights Into the Genetics of Inflammatory Bowel Disease. Gastroenterology 2011, 140(6), 1704-1712.
Cusumano CK et al, Treatment and Prevention of Urinary Tract Infection with Orally Active FimH Inhibitors. Sci. Transl. Med, 2011, 3(109), 1-22.
Darfeuille-Michaud et al. High Prevalence of Adherent-Invasive *Escherichia coli* Associated With Ileal Mucosa in Crohn's Disease. Gastroenterology, 2004, 127 (2), 412-421.
Dogan B. et al., Inflammation-associated Adherent-invasive *Escherichia coli* Are Enriched in Pathways for Use of Propanediol and Iron and M-cell Translocation. Inflamm Bowel Dis. 2014, 20(11), 1-14.
Dreux N. et al. Point mutations in FimH adhesin of Crohn's disease-associated adherent-invasive *Escherichia coli* enhance intestinal inflammatory response. PLOS Pathogens 2013, 9(1), 1-17.
Glasser AL. et al, Adherent Invasive *Escherichia coli* Strains from Patients with Crohn's Disease Survive and Replicate within Macrophages without Inducing Host Cell Death. Infection and Immunity, 2001, 60(9), p. 5529-5537.
Godon JJ. et al, Molecular Microbial Diversity of an Anaerobic Digestor as Determined by Small-Subunit rDNA Sequence Analysis. Appl. Environ. Microbiol. 1997, 63(7), 2802-2813.
Holden N. et al.,Comparative analysis of FimB and FimE recombinase activity. Microbiology 2007, 153, 4138-4149.
Klemm P., Two regulatory fim genes, fimB and fimE, control the phase variation of type 1 fimbriae in *Escherichia coli*, The EMBO journal, 1986, 5(6), 1389-1393.
Kulasekara HD et al., The molecular basis for the specificity of fimE in the phase variation of type 1 fimbriae of *Escherichia coli* K-12. 1999, Mol. Microbiol. 31(4), 1171-1181.
Molodecky NA, et al. Increasing Incidence and Prevalence of the Inflammatory Bowel Diseases With Time, Based on Systematic Review. Gastroenterology, 2012, 142, 1-51.
Moor et al., High-avidity IgA protects the intestine by enchaining growing bacteria. Nature. 2017, 544(7651), 498-502.
Mossman et al. Cutting Edge: FimH Adhesin of Type 1 Fimbriae Is a Novel TLR4 Ligand. J Immunol. 2008, 181(10), 6702-6706.
Mydock-McGrane L. et al., Mannose derived FimH antagonists a promising anti virulence therapeutic strategy for urinary tract infections and Crohn's disease. Expert Opinion on Therapeutic Patents, 2016, 26(2), 175-197.
O'Brien et al., Comparative genomics of Crohn's disease-associated adherent-invasive *Escherichia coli*. Gut, 2016, 0, 1-8.
Simpson et al., Adherent and Invasive *Escherichia coli* Is Associated with Granulomatous Colitis in Boxer Dogs. Infect Immun. 2006, 74(8), 4778-4792.
Sivignon A. et al., Development of Heptylmannoside-Based Glycoconjugate Antiadhesive Compounds against Adherent-Invasive *Escherichia coli* Bacteria Associated with Crohn's Disease. MBio 2015, 6(6), 1-9.
Sokurenko EV., Quantitative Differences in Adhesiveness of Type 1 Fimbriated *Escherichia coli* Due to Structural Differences in fimH Genes. Journal of Bacteriology, 1995, 177(13), p. 3680-3686.
Spaulding et al., Selective depletion of uropathogenic *E. coli* from the gut by a FimH antagonist. Nature 2017, 546(7659), 528-532.
Sipponen T. Crohn's Disease Activity Assessed by Fecal Calprotectin and Lactoferrin: Correlation with Crohn's Disease Activity Index and Endoscopic Findings, Inflamm. Bowel. Dis.2008, 14(1), 1-7.
Sipponen T. Endoscopic Evaluation of Crohn's Disease Activity: Comparison of the CDEIS and the SES-CD. Inflamm. Bowel. Dis., 2010, 16(12), 2131-2136.
Totsika M. et al, A FimH Inhibitor Prevents Acute Bladder Infection and Treats Chronic Cystitis Caused by Multidrug-Resistant Uropathogenic *Escherichia coli* ST131. JID, 2013, 208, 921-928.
Van der Woude and Bäumler. Phase and Antigenic Variation in Bacteria. Clin Microbiol Rev. 2004, 17(3), 581-611.
Wellens et al. Intervening with Urinary Tract Infections Using Anti-Adhesives Based on the Crystal Structure of the FimH-Oligomannose-3 Complex. PLoS ONE 2008, 3(4), p. 1-13.
Yakovenko O., Inactive conformation enhances binding function in physiological conditions. PNAS 2015, 112(32), pp. 9884-9889.
Zhang H et al., Comprehensive mutagenesis of the fimS promoter regulatory switch reveals novel regulation of type 1 pili in uropathogenic *Escherichia coli* . PNAS 2016, 113(15), pp. 4182-4187.
Ghanbarpour et al., Phylogenetic background and virulence genes of *Escherichia coli* isolates from colisepticemic and healthy broiler chickens in Iran. Tropical animal health and production, 2010, 43, 153-157.
Rahdar et al., Detection of pap, sfa, afa, foc, and fim Adhesin-Encoding operons in uropathogenic *Escherichia coli* isolates col-

(56) References Cited

OTHER PUBLICATIONS lected from patients with urinary tract infection. Jundisshapur journal of microbiolmogy, 2015, 8(8), 1-6.

Shaikh et al., Film operon variant in the emergence of enterohemorrhagic *Escherichia coli*:an evolutionary and functional analysis. FEMS microbiology letters, 2007, 273, 58-63.

Russell et al. Context dependent requirements for FimH and other canonical virulence factors in gut colonization by extraintestinal pathogenic *Escherichia coli*. bioRxiv, 2017, 1-41. doi: https://doi.org/10.1101/166108.

Russell et al. Context-dependent Requirements for FimH and Other Canonical Virulence Factors in Gut Colonization by Extraintestinal Pathogenic *Escherichia coli*, bioRxiv, 2017, 1-41. DOI: 10.1101/166108.

\* cited by examiner

ON

OFF

A

B

TOOLS FOR ASSESSING FIMH BLOCKERS THERAPEUTIC EFFICIENCY

SUMMARY OF THE INVENTION

The present invention relates to an in vitro method for predicting or assessing a therapeutic response to a FimH blocker in a subject, said method comprising the step of measuring the switch of the fim operon transcription from OFF to ON in a nucleotide fraction of a biological sample of said subject. Said subject will benefit from a treatment with a FimH blocker if the normalized amplification level of the ON position of the fim operon is superior to a reference value. It is also possible to monitor the IBD disease activity in said subject by using this biomarker. Preferably, the biological sample used in this method is a stool sample.

BACKGROUND OF THE INVENTION

The gut microbiota plays an important role in several diseases, as gut microbiota lies at the interface of the gut, the host immune system and the environment. A typical human gut microbiota comprises thousands of microbial species, among which commensal, beneficial or pathogenic bacteria. The role of each of these microorganisms is hardly described; however, it is known they change their behavior in diseased individuals in favor of the pathogenic potential of certain commensal bacteria. The microbial content of the gut is believed to weigh about 1.5 kg and to outnumber the cells of the host by 10 to 1.

Inflammatory bowel diseases are characterized by an aberrant immune response occurring in a genetically predisposed host in response to microbes and/or microbial compounds found in the gut microbiota.

Crohn's disease (CD) is a chronic inflammatory bowel disease (IBD) that may affect any part of the gastrointestinal tract from mouth to anus. The age of onset is generally between 15-30 years and it is equally prevalent in women and men. The highest prevalence is found in Europe and North America with just over 300 per 100.000 persons (Molodecky et al., 2012). CD generally leads to abdominal pain, severe diarrhea and weight disorders. The disease is of unknown etiology and multifactorial: environmental factors, host genetics and gut microbiome have all been shown to impact the risk of disease and its severity (Cho et al., 2011). The clinical diagnosis of CD is supported by serologic, radiologic, endoscopic, and histologic findings.

Ulcerative colitis (or UC) is another form of inflammatory bowel disease (IBD). Ulcerative colitis is a form of colitis, a disease of the colon (the largest portion of the large intestine), that includes characteristic ulcers, or open sores. The main symptom of active disease is usually constant diarrhea mixed with blood, of gradual onset.

Of the bacteria that may play a role in the pathogenesis of these diseases, a pathotype of *E. coli*, called "AIEC" for "adherent-invasive *Escherichia coli*", has been strongly implicated (Boudeau et al., 1999). AIEC are able to adhere to the intestinal epithelium and colonize gut mucosa where they participate to IBD onset. More precisely, AIEC were found to be associated with ileal mucosa in 36.4% of CD patients compared with 6.2% of controls, suggesting that these bacteria are involved in CD pathogenesis (Darfeuille-Michaud et al., 2004; Dreux N. et al., 2013).

AIECs have also been demonstrated to be implicated in inflammatory bowel diseases of animals such as dogs and cats, in particular in connection with animals suffering from CD or from granulomatous colitis (also called histiocytic ulcerative colitis), a disease close to the corresponding human ulcerative colitis (Simpson et al., 2006).

Therefore, this has been of crucial importance to elaborate a strategy to efficiently eradicate these bacteria from the digestive and/or urinary tract.

*E. coli*'s adhesion to mucosal epithelial cells is mediated by proteinaceous, rod-like organelles that are called type-1 fimbriae. Type-1 fimbriae carry an adhesin at the edge of a flexible tip fibrillum. This adhesin, FimH, is a lectin having a strong affinity for highly mannosylated glycoproteins (Bouckaert J. et al., 2006).

The type 1 pili interact with glycoproteins such as CEACAM6 (Barnich et al 2007; Barnich et al., 2010), TLR4 (Mossman et al., 2008) or GP2 (Chassaing et al., 2011) in a mannose-associated manner. CEACAM6 and TLR4 receptors are upregulated by inflammatory cytokines in CD patients with ileal disease. The binding of FimH to TLR4 induces the production of TNFα, IL-6 and IL-8 in the gut, independently of LPS. Additionally, FimH binding to GP2 on the surface of M cells in the Peyer's patches allow AIEC to enter into the lamina propria. The subsequent phagocytosis of the AIEC by the macrophages further contributes to the chronic production of TNFα. A vicious cycle of proinflammatory cytokine release is produced by the TNFα driven overexpression of CEACAM6 and TNFα driven increase in M-cell development (Bennett et al, 2016). Thus, FimH appears as a critical factor that not only stimulates direct production of pro-inflammatory cytokines from the gut epithelium, but plays an important role in the invasion of the lamina propria.

Not only AIECs, but a number of other proteobacteria express FimH at their surface. These proteobacteria are for example responsible for urinary tract infections.

It is also of crucial importance to elaborate a strategy to efficiently detect these FimH-expressing proteobacteria in infected subjects in order to eventually eradicate them from their digestive and/or urinary tract, e.g., by treating said subjects with FimH blockers.

Yet, such identification is currently viewed as a difficult task.

The AIEC pathovar has originally been defined by in vitro cell-line assays examining specific bacteria/cell interactions (Darfeuille-Michaud et al., 2004). Since then, the only way to identify them has been to isolate bacterial cells from patient samples obtained by invasive proceedings (mostly during biopsies of mucosal tissues or lymph nodes), cultivate them for several weeks, and conduct bacteria/cell interaction assays, for example with epithelial cells or macrophages in which AIECs are known to survive and replicate (Glasser A L. et al., 2001; Bringer M A. et al., 2006). These protocols are however invasive, time-consuming, costly, and hardly reproducible across laboratories. They can, therefore, not be used routinely as biomarkers or diagnostics.

To date the search for molecular markers of AIEC has failed (O'Brien et al., 2016). This could be due to the lack of a standardised and highly reproducible protocol as just mentioned, but could also be explained by the fact that AIEC are not under control by a single gene but rather under complex genetic regulation and/or under environmental control.

Thus, there is still a need for non-invasive and sensitive diagnostic tests to easily and reliably detect the expression of FimH in proteobacteria from infected subjects.

Type 1 fimbriae are encoded by the fim operon, and their expression is phase variable, depending on an invertible DNA element (the fimS region) that is located upstream of the fim operon and contains the fim promoter (Barnich et al., 2003). More precisely, the fimS region is the intergenic region that spans between the fimE and fimA genes. Two tyrosine recombinases, FimB and FimE, are known to control the orientation of the fimS-invertible region by a switch mechanism as shown on FIG. 1. FimB has bidirectional activity but predominantly switches fim operon transcription from OFF to ON, while FimE exclusively mediates ON to OFF phase switching (Holden et al., 2007; Kulasekara et al., 1999). This switch is known to occur at a high frequency. This so-called "FimS switch mechanism" regulates in bacteria the expression of the fim operon and of the fimH gene in particular (Burns et al., 2000; Zhang et al., 2016).

DETAILED EMBODIMENTS OF THE INVENTION

Using a large collection of *E. coli* bacterial strains isolated from IBD patients and controls that have been well characterized and fully sequenced, the present Inventors were able to isolate bacterial strains that aggregate efficiently to FimH blockers and therefore express a sufficient amount of the FimH lectin at their surface to bind a FimH blocker. Based on these strains, they searched and identified an easy, reproducible and quantitative test for measuring in an ex vivo sample the number of bacteria actually expressing the FimH lectin at their surface (and not only carrying the FimH gene).

The molecular signature identified by the inventors is focused on the FimH molecular pattern and, more precisely, on the "FimS switch mechanism" switching the fim operon transcription from OFF to ON, leading to the expression of the FimH lectin at the surface of proteobacteria. The inventors herein show that this molecular signature can be detected by conventional means (such as qPCR). It can be obtained rapidly after the sample is collected. It is quantitative and reproducible. Last but not least, it works very well on whole stool samples that have not undergone any purification/separation.

Because the switch mechanism that occurs in the ileum is known to revert extremely fast from the ON position to the OFF position, this test surprisingly appeared to be able to detect the ON position of the switch in a sensitive and quantitative manner when applied on whole raw stool samples that have been collected from patients. This is of primary importance, since it means that the practician does not need to analyze endoscopic biopsies, and that non-invasively obtained stool samples are sufficient. Moreover, as the test of the invention does not require to isolate or cultivate the bacteria present in the sample, it is far quicker and more reliable than the protocols of the prior art.

This is also very surprising. As a matter of fact, AIEC have been reported to be significantly increased in the ileal mucosa of CD patients versus controls but not in the stool where they were found at similar low amounts as in the controls. One possible explanation is that expressing FimH is energy consuming for the bacteria so that FimH expression will be triggered by the environment only when there is a real need/benefit for adhesion. Therefore, in the stool and in a healthy gut the *E. coli* bacteria will in majority not express the FimH lectin (OFF position of the fim operon). Consequently, no method has ever been proposed to detect FimH-expression in stool samples.

The present inventors fortunately fulfilled this need, by proposing a molecular signature that can be used to detect FimH-expressing bacteria in stool samples of infected patients and therefore assess the virulence of these bacteria.

In addition, the molecular signature of the invention enables to prognose the effect of therapeutic interventions that aimed at blocking the FimH-based interaction between FimH-expressing bacteria and gut mucosa. Eventually, it enables to design tailored treatments for particular subsets of patients hosting high amounts of FimH-expressing bacteria. Personalized treatment will now be possible by prescreening the samples of the patients for detecting the molecular signature of the invention before administering the FimH blocker treatments.

As used herein, the term "proteobacteria" designates Gram-negative bacteria including, among others, *Escherichia, Klebsiella, Shigella, Salmonella, Vibrio, Yersinia* and *Helicobacter* bacteria. The proteobacteria are divided into six classes with validly published names, referred to by the Greek letters alpha (a) through epsilon (E) and the *Acidithiobacillia* and *Oligoflexia*. Alphaproteobacteria include *Brucella, Rhizobium, Agrobacterium, Caulobacter, Rickettsia*, and *Wolbachia* bacteria. Beta proteobacteria include *Bordetella, Ralstonia, Neisseria*, and *Nitrosomonas* bacteria. Gammaproteobacteria include *Escherichia, Shigella, Salmonella, Yersinia, Buchnera, Haemophilus, Vibrio*, and *Pseudomonas* bacteria. Epsilonproteobacteria include *Helicobacter, Campylobacter*, and Wolinella bacteria.

As used herein, the term "FimH expressing proteobacteria" designates proteobacteria as defined above, expressing a high amount of functional FimH lectin at their surface. Preferably, said FimH expressing proteobacteria are pathogenic. In particular, they are Gammaproteobacteria expressing high amount of functional FimH lectin at their surface. In contrast, the term "FimH carrying bacteria" relates to any bacteria carrying the fimH gene in their genome, but that do not necessarily express it as proteins presented at the surface of the bacteria.

The purpose of the invention is to detect patients hosting high amounts of gut bacteria expressing high amount of functional FimH lectin at their surface, simply by using molecular means and non-invasively obtained samples such as stool samples. These patients will indeed benefit from a FimH-blocker treatment, and his/her disease can be followed accordingly.

A "high amount of functional FimH lectin" expressed by bacteria at their surface can be assessed by aggregation tests or adhesion tests such as those disclosed in the art (Yakovenko O., 2015; Sokurenko EV 1995). The amount of expressed functional FimH lectin is said to be "high" when aggregation of the tested bacteria is observed as opposed to reference bacteria that are known not to express any functional FimH lectin at their surface and do not aggregate. The *E. coli* K12 strain, alternatively the deltaFimH LF82 strain which is the LF82 strain lacking the FimH gene, can for example be used as reference bacteria. The previously described AAEC191A strain can also be used as reference bacteria, because they do not express the FimH lectin at their surface (Sokurenko E V et al., 1995).

In one aspect, the present invention relates to an in vitro method for detecting the presence of FimH expressing proteobacteria in a biological sample of a subject, said method comprising the steps of:
 a) optionally isolating the nucleotide fraction of said biological sample,
 b) detecting the expression of the fimH gene in said nucleotide fraction, preferably by qPCR.

As mentioned above, this method can be used for identifying subjects hosting high amounts of FimH expressing proteobacteria in their gut.

As used herein, the term "subject" refers to a mammal, preferably a human. More preferably, said mammal or human has been diagnosed to suffer from a disease relying on FimH-expressing proteobacteria infection, such as a urinary tract infection (UTI) or an IBD (Crohn's disease or Ulcerative Colitis, in adults or in children). More preferably, said subject is a human being suffering from the Crohn's disease or having underwent a surgical operation as a Crohn's disease treatment. Alternatively, said subject is a human being suffering from a urinary tract infection.

As used herein, the term "biological sample" designates any sample collected from a subject, that may contain bacterial cells. It can be a serum sample, a plasma sample, a urine sample, a blood sample, a stool sample, a lymph sample, or a biopsy. In the context of the invention, said biological sample is preferably a stool sample or a mucosal biopsy.

As "biological sample", it is also possible to use surgical specimens obtained during surgical operations and stored in a bio-bank, as the presence of AIECs in these specimens is known to be representative of a high risk for severe endoscopic post-operative recurrence of Crohn's disease (Barnich N. et al, AGA Abstract 2017).

The term "biological sample" may also designate a bacterial isolate purified from said samples. Bacterial purification is well known in the art. Any appropriate method can be used in this respect.

As used herein, the "expression" of a gene (here the fimH gene) is the process by which information from a gene is used in the synthesis of a functional gene product (here the FimH lectin). Gene expression can be detected by determining the presence of the corresponding mRNA and/or the gene products at the protein level, by conventional means.

The expression of a gene can also be assessed in the context of the invention by measuring the abundance of the gene in terms of "copy number". As a matter of fact, when a core gene is considered (e.g., the fimH gene), its abundance correlates with the its expression. The higher its copy number is, the more expressed the gene is.

Preferably, the level of expression of the fimH gene as concluded by the molecular methods of the invention can be confirmed by functional assays showing that the FimH lectin is actually present at the surface of the bacterial cells.

As shown in the experimental part below, the step b) of said method is preferably performed by analyzing the level of expression of the mRNA of the fimH gene, or by detecting the switch of the fim operon transcription from OFF to ON, or the abundance of the fimH gene, in the nucleotide fraction of said biological sample.

Therefore, as used herein, the term "nucleotide fraction" designates double-stranded DNA, single-stranded DNA and products of transcription of said DNAs, and also the nucleotide sequences which hybridize with them, that can be isolated or retrieved from a stool sample. As such, this term is similar to the terms "nucleic acid", "nucleic acid sequence" or "sequence of nucleic acid", "polynucleotide", "oligonucleotide", "polynucleotide sequence", and "nucleotide sequence", which will be used equally in the present description. It should be understood that the present invention does not relate to the genomic nucleotide sequences in their natural chromosomal environment, i.e., in their natural state. It involves sequences which have been "isolated" and/or "purified", i.e., they have been removed, directly or indirectly, from their natural chromosomal environment, for example by copying, synthetizing, etc.

Methods to isolate nucleotide fractions are known in the art. Some DNA isolation techniques are described in, for example, EP 145,356, EP 240,191, and EP 245,945, all of which use an alcohol and an enzymatic protein decomposer in certain sequences of steps. Standard nucleic acid extraction techniques are disclosed in Maniatis et al, Molecular Cloning: A Laboratory Manual (New York: Cold Spring Harbor Laboratory, 1982), pp. 280-281 and, more recently, in Ayoib A. et al, 2017.

Measuring the level of expression of the mRNA of the fimH gene can be done by any conventional means, such as RT-qPCR. Isolation of mRNA from a sample is also widely disclosed, and commercial kits are available, depending on the nature of the sample. Amplification of DNA by different means has been thoroughly disclosed in the art.

Mammal DNA can be distinguished from microbial DNA by any conventional mean, such as detection of CpG methylation or of the bacterial 16S ribosomal DNA. It is also possible to use qPCR targeting the ALU (STR) repeat regions in human DNA, or the Beta-globulin, Beta-actin, and hTERT genes. Nanostring technologies could be also useful.

The most commonly used methods known in the art for the quantification of DNA copies in a sample include Northern blotting, in situ hybridization and PCR-based methods, such as quantitative polymerase chain reaction (qPCR). Alternatively, antibodies may be employed that can recognize sequence-specific duplexes, including DNA duplexes or DNA-protein duplexes. Representative methods for sequencing-based analysis include chain-termination methods, shotgun sequencing methods, de novo sequencing, next generation sequencing methods (including Massively Parallel Signature Sequencing (MPSS), Polony sequencing, 454 pyrosequencing, Illumina (Solexa) sequencing, SOLiD sequencing, Ion semiconductor sequencing, DNA nanoball sequencing, Helioscope single molecule sequencing, Single molecule real time (SMRT) sequencing, RNAP sequencing, Nanopore DNA sequencing, Sequencing by hybridization and Microfluidic Sanger sequencing).

qPCR is a well-known technology whose conditions are thoroughly explained in the notice of commercial kits (SIGMA-ALDRICH, QIAGEN, . . . ). It is a routine task for the skilled person to identify the appropriate conditions to be used once the target regions or the primers are known. Any qPCR method can be used for amplifying and detecting the amplification level of the targeted regions in the present invention. SYBR GREEN qPCR which has been used by the inventors in the experimental part below, is currently the preferred amplification method to detect the expression level of FimH by means of the molecular signature according to the present invention.

To implement the methods of the invention, it is also possible to use multiplexed technologies such as the Nanostring's nCounter technology (for example described in U.S. Pat. No. 7,473,767).

As disclosed herein, the terms "in vitro" and "ex vivo" are equivalent and refer to studies or experiments that are conducted using samples (e.g. cells or population of cells present in a stool sample) that have been isolated from their usual host organisms (e.g. animals or humans). Such samples can be directly used in the methods of the invention, without further processing. Alternatively, bacterial cells may be purified before their nucleotide fraction is used in the methods of the invention. These methods can be for example reduced to practice in laboratory materials such as tubes, flasks, wells, eppendorfs, etc. In contrast, the term "in vivo" refers to studies that are conducted in whole living organisms.

As used herein, the term "stool sample" designates a sample of whole stool that has been collected non-invasively after defaecation in an appropriate recipient. Said recipient was clean, and preferably devoid of any contaminating agents (bacteria, material, virus, etc.). Particular recipients and protocols can be used in this aim, such as those described in EP 1 371 964, EP 1986 006, or FR1456674.

It is not necessary to exclude, purify or extract particular cells from this sample, all the DNA contained in the raw sample can be used in the methods of the invention.

In a first preferred embodiment, the fimH surface level of the bacterial cells is assessed by measuring the switch of the fim operon transcription from OFF to ON in the DNA of the fimH gene. DNA is preferably extracted from said stool sample by using a convenient commercial extraction protocol such as those proposed by MOBIO, Qiagen or Zymo. Of note, the bacterial DNA and the host DNA do not need to be physically separated for reducing the methods of the invention to practice.

The present invention more precisely relates to an in vitro method for detecting the presence of FimH expressing proteobacteria in a stool sample of a subject, or for identifying subjects hosting high amounts of FimH expressing proteobacteria in their gut, said method comprising the steps of:
a) isolating the nucleotide fraction of the stool sample,
b) detecting the expression of the fimH gene by measuring by qPCR the switch of the fim operon transcription from OFF to ON in said nucleotide fraction.

The switch of the fim operon transcription from OFF to ON has been characterized long ago (Klemm P., 1986). However, since then, it has only been studied in mutant cells or systems that have been engineered so as to express molecular identifiers (see for example Zhang H. et al., 2016). This kind of detection is not possible in natural biological samples such as stool samples. The only reliable means proposed in the art to detect the fim operon switch in naturally occurring bacteria was to detect directly the expression of the FimH lectin at the surface of the bacteria. This detection required first to isolate the bacteria from the sample (generally biopsies), then to cultivate them in order to amplify their number, and finally to use anti-FimH antibodies or conduct aggregation tests with FimH antagonists. Yet, these methods were time-consuming and not quantitative at all, due to the ex vivo expansion of the bacterial cells. Moreover, as mentioned above, they were not transposable to stool samples in which the amount of FimH-expressing bacteria is very low as compared with the amount of total bacteria, because multiple bacteria coexist within a same sample.

Despite all these prejudices, the inventors managed to identify a quantitative test enabling to assess the amount of FimH-expressing bacteria in a stool sample of a subject. More precisely, they identified a molecular signature that correlates with the expression of the FimH lectin at the surface of the proteobacteria (as revealed by aggregation tests) and that can be detected in stool samples.

In this particular embodiment, this molecular signature relies on detecting the fimS switching mechanism by using appropriately chosen molecular tools. Particularly, it requires to use primers targeting specific regions within the FimS, the FimA and FimE regions, so as to detect the relative amounts of ON and OFF positions within a sample. Also, it can use probes hybridizing specifically to the switch regions in the FimS nucleotide sequence.

The FimE-FimS-FimA OFF position has the nucleotide sequence as shown in SEQ ID NO:13.

The FimE-FimS-FimA ON position has the nucleotide sequence as shown in SEQ ID NO:14.

The FimE nucleotide sequence in the OFF position has the sequence SEQ ID NO:15. The FimS nucleotide sequence in the OFF position has the sequence SEQ ID NO:16. The FimA nucleotide sequence in the OFF position has the sequence SEQ ID NO:17.

The FimE nucleotide sequence in the ON position has the sequence SEQ ID NO:18. The FimS nucleotide sequence in the ON position has the sequence SEQ ID NO:19. The FimA nucleotide sequence in the ON position has the sequence SEQ ID NO:20.

The "switch regions" within the FimS gene are those having the sequence SEQ ID NO:9 and SEQ ID NO:10.

The nucleotide regions of SEQ ID NO:11 (ttggggcca) and SEQ ID NO:12 (tggccccaa) correspond to Inverted Repeat Regions located in the FimS gene located respectively in SEQ ID NO:27 and SEQ ID NO:30.

In a preferred embodiment, measuring the switch of the fim operon transcription from OFF to ON in the methods of the invention is performed by targeting one or more of these particular regions, e.g., by using primers or probes specifically amplifying or hybridizing one or more of these regions.

More particularly, the following nucleotide regions can be targeted:
Within the fimE gene: SEQ ID NO:21, SEQ ID NO:22, SEQ ID NO:23, SEQ ID NO:24, SEQ ID NO:25, and/or SEQ ID NO:26,
Within the fimS gene: SEQ ID NO:27, SEQ ID NO:28, SEQ ID NO:29, SEQ ID NO:30, SEQ ID and/or NO:31,
Within the fimA gene: SEQ ID NO:32 and/or SEQ ID NO:33.

Primers amplifying partially or totally a nucleotide region having a sequence chosen in the group consisting of: SEQ ID NO:15-17 (OFF position), SEQ ID NO:18-20 (ON position), and SEQ ID NO:21-SEQ ID NO: 33, are encompassed within the present invention.

Primers amplifying partially or totally a nucleotide region containing or consisting of the specific "switch regions" SEQ ID NO: 9 and/or SEQ ID NO:10 or more specifically to the Inverted Repeat Regions of SEQ ID NO:11 (ttggggcca) and/or SEQ ID NO:12 (tggccccaa) are also encompassed within the present invention.

Probes hybridizing to the specific "switch regions" SEQ ID NO: 9 and/or SEQ ID NO:10 or more specifically to the Inverted Repeat Regions of SEQ ID NO:11 (ttggggcca) and/or SEQ ID NO:12 (tggccccaa) are also encompassed within the present invention.

In a particular embodiment, homologous regions can be targeted. In the context of the invention, "homologous regions" refer to nucleotide regions whose sequences have, with respect to the reference nucleic acid sequence to which they refer (e.g., SEQ ID NO:9 to 33), certain modifications, such as in particular a deletion, a truncation, an extension, a chimeric fusion and/or a mutation, in particular a point mutation. In a particular embodiment, the nucleotide sequences of these homologous regions share at least 80%, preferably 90% or 95%, identity with the reference nucleic acid sequence to which they refer (e.g., SEQ ID NO:9 to 33).

For the purpose of the present invention, the percentage of identity between two nucleic acid sequences is intended to refer to a percentage of nucleotides which is identical between the two sequences to be compared, obtained after the best alignment, this percentage being purely statistical and the differences between the two sequences being distributed randomly and throughout their length. Sequence comparisons between two nucleic acid sequences are traditionally carried out by comparing these sequences after having optimally aligned them, said comparison being carried out by segment or by "window of comparison" in order to identify and compare local regions of sequence similarity. The optimal alignment of the sequences for comparison can be produced, besides manually, by means of the global homology algorithm of Needleman and Wunsch (1970) [J. Mol. Biol. 48:443]. The percentage of identity is calculated by determining the number of identical positions for which the nucleotide is identical between the two sequences, dividing this number of identical positions by the total number of positions and multiplying the result obtained by 100 so as to obtain the percentage of identity between these two sequences. For example, the needle program available on the site ebi.ac.uk, may be used, the parameters used being those given by default (in particular for the parameters "Gap open":10, and "gap extend":0.5; the matrix chosen being, for example, the "BLOSUM 62" matrix proposed by the program), the percentage of identity between the two sequences to be compared being calculated directly by the program.

The following qPCR primers have been tested by the Inventors (see also the experimental part below):

| Name of the primer | Sequence of the primer | SEQ ID NO: |
|---|---|---|
| p1 | GTAATGCTGCTCGTTTTGCC | SEQ ID NO: 1 |
| p2 | CATATAGCGGAGGTGATGTGAA | SEQ ID NO: 2 |
| P3 | TGCGCGATGCTTTCCTCTAT | SEQ ID NO: 3 |
| p4 | GCGCAAGCGGCGTTA | SEQ ID NO: 4 |
| p5 | CGGATTATGGGAAAGAAAT | SEQ ID NO: 5 |
| p6 | TCAAACAGTTAGATGCTTT | SEQ ID NO: 6 |
| p7 | CGATGCTTTCCTCTATGA | SEQ ID NO: 7 |
| p8 | TTGTTTTGTCAACGAGTT | SEQ ID NO: 8 |

The relative position of these primers is disclosed in FIG. 3. Moreover, their sequence is disclosed in the enclosed sequence listing under appropriate format.

In a more preferred embodiment, measuring the switch of the fim operon transcription from OFF to ON in the methods of the invention is performed by using the primers of SEQ ID NO:1-8.

In an even more preferred embodiment, measuring the expression of the FimH lectin is performed by amplifying the nucleotide fractions contained in the sample with the primers of SEQ ID NO:1, SEQ ID NO:2, SEQ ID NO:3, and SEQ ID NO:4 or with the primers of SEQ ID NO:5, SEQ ID NO:6, SEQ ID NO:7 and SEQ ID NO:8 that highlight the ON and the OFF positions of the fimH operon. The two primer pairs [SEQ ID NO:5; SEQ ID NO:7] and [SEQ ID NO:6; SEQ ID NO:8], or the two primer pairs [SEQ ID NO:1; SEQ ID NO:3] and [SEQ ID NO:2; SEQ ID NO:4] can be used more specifically for detecting the ON position. Preferably, the primer pairs [SEQ ID NO:5; SEQ ID NO:7] and [SEQ ID NO:6; SEQ ID NO:8] are used for detecting the ON position of the fimH operon. More preferably, the primer pair [SEQ ID NO:5; SEQ ID NO:7] is used for detecting the ON position of the fimH operon. The two primer pairs [SEQ ID NO:5; SEQ ID NO:8] and [SEQ ID NO:7; SEQ ID NO:8], or the two primer pairs [SEQ ID NO:1; SEQ ID NO:2] and [SEQ ID NO:3; SEQ ID NO:4] can be used more specifically for detecting the OFF position. Preferably, the primer pairs [SEQ ID NO:5; SEQ ID NO:8] and [SEQ ID NO:7; SEQ ID NO:8] are used for detecting the OFF position of the fimH operon. More preferably, the primer pair [SEQ ID NO:5; SEQ ID NO:8] is used for detecting the OFF position of the fimH operon.

The amplification level observed with these pairs of primers can then be normalized with the amounts of total DNA contained in the sample, or the amount of total bacteria (excluding the amount of host DNA) or only the amount of FimH expressing bacteria. This can be done by concomitantly amplifying bacterial housekeeping genes that will reflect the absolute amount of bacteria contained in the sample or by using a conserved region of the FimH gene. It is also possible to normalize the results generated by the qPCR of the invention by expressing all the results in DNA copy number per µL.

When the normalized amplification level of the fim operon measured by using the pairs of primers dedicated to the ON position is superior to a reference value, then the fim operon is in position ON, what reflects a high level of expression of FimH at the surface of the bacterial cells present in the sample, so that the tested subject hosts a high amount of FimH expressing bacteria in his/her gut, and will therefore be sensitive to a FimH blocker.

When the normalized amplification level of the fim operon measured by using the pairs of primers dedicated to the OFF position is superior to a reference value, then the fim operon is in position OFF, what reflects a low level of expression of FimH at the surface of the bacterial cells present in the sample, so that the tested subject hosts a low amount of FimH expressing bacteria in his/her gut, and will therefore be unresponsive to a FimH blocker.

As used herein, the term "reference value" (or "control value") refers to a specific value or predetermined value, which can take a variety of forms. It can be a single cut-off value, such as a median or mean. It can be a single number, equally applicable to every sample individually, or it can vary, according to specific types of sample or subpopulations of patients. This reference value can be easily determined by the skilled person by using reference bacteria that are known not to express the FimH lectin at their surface (e.g., bacteria from the K12 or AAEC191A strains). It can be also determined in stool samples of healthy subjects. K12 bacteria have been described in the art, for example in Boudeau et al., 2001, or in O'Brien et al, 2016.

When stool samples are used, typical reference values for the normalized amplification level of the ON position are of 1%, 2%, 3%, 4% 5%, 10%, 15%.

When stool samples are used, typical reference values for the normalized amplification level of the OFF position are of 1%, 2%, 3%, 4% 5%, 10%, 15%.

To go further, the inventors identified that it is also possible to use the ON/OFF ratio or an ON/(ON+OFF) ratio provided in the samples in order to assess the surface level of FimS in the bacterial contained in these samples.

They therefore propose particular systems of primers that enable to evaluate the ON/OFF ratio or an ON/(ON+OFF) ratio of FimS in bacterial samples as well as in stool samples. The systems of primers are the following: [SEQ ID NO:3; SEQ ID NO:4] or [SEQ ID NO:7; SEQ ID NO:8] for the OFF position, and [SEQ ID NO:1; SEQ ID NO:3] or [SEQ ID NO:5; SEQ ID NO:7] for the ON position. The two primer pairs [SEQ ID NO:5; SEQ ID NO:7] and [SEQ ID NO:6; SEQ ID NO:8], or the two primer pairs [SEQ ID NO:1; SEQ ID NO:3] and [SEQ ID NO:2; SEQ ID NO:4]

can be used more specifically for detecting the ON position. Preferably, the primer pairs [SEQ ID NO:5; SEQ ID NO:7] and [SEQ ID NO:6; SEQ ID NO:8] are used for detecting the ON position. More preferably, the primer pair [SEQ ID NO:5; SEQ ID NO:7] is used for detecting the ON position. The two primer pairs [SEQ ID NO:5; SEQ ID NO:8] and [SEQ ID NO:7; SEQ ID NO:8], or the two primer pairs [SEQ ID NO:1; SEQ ID NO:2] and [SEQ ID NO:3; SEQ ID NO:4] can be used more specifically for detecting the OFF position.

When appropriately combined, these pairs of primers enable to determine the ON/OFF ratio of the fim operon. An ON/OFF ratio or an ON/(ON+OFF) ratio superior to a reference value closely reflects a high level of expression of FimH at the surface of said bacterial cells and therefore the ability of the bacterial cells present in the sample to aggregate a FimH blocker.

As shown in the experimental part below, FimH expressing bacteria such as LF82 AIECs have a typical ON/(ON+OFF) ratio which is superior to 30%, whereas non-aggregative cells have a typical ON/(ON+OFF) ratio inferior to 5%. Therefore, the reference value associated with isolated strains can be of about 15%.

When stool samples are used, typical reference values for the ON/(ON+OFF) ratio are of 1%, 2%, 3%, 4%, 5%, 10% and 15%.

When stool samples are used, typical reference values for the ON/OFF ratio are of 1%, 2%, 3%, 4%, 5%, 10% and 15%.

In a more preferred embodiment, measuring the switch of the fim operon transcription from OFF to ON in the methods of the invention is therefore performed by targeting the above-mentioned particular regions using these particular pairs of primers.

In a preferred embodiment, the amplification level for the OFF position is detected by using the primers pair [SEQ ID NO:3; SEQ ID NO:4], and the amplification level for the ON position is detected by using the primers pair [SEQ ID NO:2; SEQ ID NO:4].

In a preferred embodiment, the amplification level for the OFF position is detected by using the primers pair [SEQ ID NO:3; SEQ ID NO:4], and the amplification level for the ON position is detected by using the primers pair [SEQ ID NO:1; SEQ ID NO:3].

In a preferred embodiment, the amplification level for the OFF position is detected by using the primers pair [SEQ ID NO:1; SEQ ID NO:2], and the amplification level for the ON position is detected by using the primers pair [SEQ ID NO:1; SEQ ID NO:3].

In a preferred embodiment, the amplification level for the OFF position is detected by using the primers pair [SEQ ID NO:1; SEQ ID NO:2], and the amplification level for the ON position is detected by using the primers pair [SEQ ID NO:2; SEQ ID NO:4].

In a preferred embodiment, the amplification level for the OFF position is detected by using the primers pair [SEQ ID NO:7; SEQ ID NO:8], and the amplification level for the ON position is detected by using the primers pair [SEQ ID NO:6; SEQ ID NO:8].

In a preferred embodiment, the amplification level for the OFF position is detected by using the primers pair [SEQ ID NO:7; SEQ ID NO:8], and the amplification level for the ON position is detected by using the primers pair [SEQ ID NO:5; SEQ ID NO:7].

In a preferred embodiment, the amplification level for the OFF position is detected by using the primers pair [SEQ ID NO:5; SEQ ID NO:8], and the amplification level for the ON position is detected by using the primers pair [SEQ ID NO:5; SEQ ID NO:7].

In a more preferred embodiment, the amplification level for the OFF position is detected by using the primer pair [SEQ ID NO:5; SEQ ID NO:8], and the amplification level for the ON position is detected by using the primer pair [SEQ ID NO:6; SEQ ID NO:8].

A normalized amplification level of ON or an ON/OFF ratio or an ON/(ON+OFF) ratio superior to said reference values is of predictive value for a FimH blocker treatment, because it enables to distinguish patients who have a high probability of clinical benefit (because the bacteria cells express the FimH lectin that will be blocked by the FimH blocker) from those who will take no benefit from said treatment (because they do not host bacteria whose behavior is sensitive to said treatment).

More precisely, when the normalized amplification level of ON or the ON/OFF or ON/(ON+OFF) ratio which is calculated by the above-means is higher than the said reference values, then it can be concluded that the tested sample contains a considerable amount of FimH-expressing bacteria, and that the patient from which the sample has been collected will benefit from a treatment with FimH blockers.

On the contrary, when the normalized amplification level of ON or the ON/OFF or ON/(ON+OFF) ratio is lower than the said reference values, then it can be concluded that the tested sample contains a low amount of FimH-expressing bacteria, and that the patient from which the sample has been collected hosts too few of these bacteria to benefit from a treatment with FimH blockers. Healthy subjects are in this category.

In a second preferred embodiment, the fimH lectin surface level of the bacterial cells is assessed by measuring the abundance of the fimH gene in the nucleotide fraction of the biological sample collected from the subjects.

Indeed, the present inventors have shown that the copy number of the fimH gene measured in a stool sample of a subject correlates with the amount of gut bacterial cells (isolated from biopsies) aggregating the FimH blocker EB8018, therefore expressing a lectin at their surface. It is therefore possible, simply by measuring the abundance of the fimH gene in a stool sample of a subject, to identify if and to what extend the bacteria present in the gut of said subject carry high amount of the FimH lectin at their surface, and will therefore be—or not—sensitive to a treatment with a FimH blocker.

This result is unexpected, since it was thought that the abundance of the fimH gene detected in stool was not enhanced in patients suffering from IBDs, even though AIECs were known to be significantly increased in the ileal mucosa of CD patients versus controls.

Example 6 below (and FIG. 7) shows that a qPCR assay performed on the fimH gene of SEQ ID NO:34 leads the skilled person to identifying and/or discriminating the subjects hosting fimH expressing bacteria.

By using for example, the primer pairs of SEQ ID NO:35-36, SEQ ID NO:37-38, SEQ ID NO:39-40, it is therefore possible to detect with a high reliability the presence of FimH expressing proteobacteria in the gut of a subject.

By using for example, the probes of SEQ ID NO:41-43, it is also possible to detect with a high reliability the presence of FimH expressing proteobacteria in the gut of a subject.

By "gene abundance", it is herein meant the absolute or relative amount of the tested genes. "Absolute amount" (or "absolute abundance") of a gene designates the total number of copies of said gene in a define volume of the tested sample, whereas "relative amount" (or "relative abundance") of a gene designates the total number of copies of said gene relative to the total amount of genes or alternatively the total number of copies of said gene relative to the amount of a single reference gene or preferably a combination of reference genes present in the tested sample. Ubiquitous genes, such as genes essential for the survival of the organism like DNA polymerases or genes coding for proteins involved in glucose metabolism, are good candidates for reference genes in metagenomic studies.

The methods of the invention preferably require the measurement of the absolute amount of the gene, e.g., the total number of copies by µL, as classically provided by nanostring or qPCR technologies.

When the abundance of the fimH gene measured by using the appropriate pairs of primers is superior to a reference value, then it can be concluded that the tested subject hosts a high amount of FimH expressing bacteria in his/her gut, and will therefore be sensitive to a FimH blocker.

When the abundance of the fimH gene measured by using the appropriate pairs of primers is inferior to a reference value, then it can be concluded that the tested subject hosts a low amount of FimH expressing bacteria in his/her gut, and will therefore be poorly sensitive (or even unresponsive) to a FimH blocker.

The abundance measured with these pairs of primers is usually normalized with the amounts of total DNA contained in the sample, or with the amount of total bacteria (excluding the amount of host DNA). This can be done by concomitantly amplifying bacterial housekeeping genes that will reflect the absolute amount of bacteria contained in the sample.

When stool samples are used, typical reference values for the abundance of the FimH gene are of 1%, 2%, 3%, 4% 5%, 10%, 15%.

In a third preferred embodiment, the two molecular markers disclosed above are combined so as to calculate the ratio called "FimS ON/FimH". This ratio has been found by the inventors to be highly valuable to detect subjects hosting high amounts of AIECs in their gut.

To calculate this ratio, the two molecular markers "FimS ON" and "FimH" are detected and quantified as disclosed above, i.e., by using particular primer sets hybridizing either with the switch region, or the "ON" regions, or with the fimH gene of SEQ ID NO:34. The signals are then normalized and the ratio is calculated before being compared to a reference value.

Said reference value is for example the mean abundance of the fimH gene of SEQ ID NO:34 measured in stool samples of at least two healthy subjects.

When the ratio FimS ON/FimH is superior to this reference value, then it can be concluded that the tested subject hosts a high amount of FimH expressing bacteria in his/her gut, and will therefore be sensitive to a FimH blocker. Thanks to the methods of the invention, it will be now possible to easily identify the patients that will effectively (or more effectively) benefit from a FimH blocker treatment. In other terms, it will be possible to evaluate or predict the therapeutic response of a subject when a FimH blocker is administered.

As used herein, the term "FimH blocker" (or "FimH inhibitor" or "FimH antagonist") designates any compound that is able to interfere with the interaction of the FimH lectin and the mannose residues from glycosylated proteins on the epithelial cells of the gut. When this interaction is weakened or abolished, so does the bacteria invasion of the gut mucosa in the treated patient. Consequently, the cascade of inflammatory reaction is impeded or prevented and the inflammatory disease is alleviated.

A number of efficient mannose derivatives having this interfering activity have been described. They are all herewith encompassed:

Heptylmannose (HM) is one of the most efficient FimH antagonists and a potent in vitro AIEC adhesion inhibitor (Bouckaert et al., 2005, Bouckaert et al., 2013). HM is generally used as a reference in the antiadhesive assays but proved disappointing in vivo. Indeed, millimolar concentrations are required to observe a significant bacterial load reduction in a cystitis murine model (Wellens et al., 2008) and gave no effect with AIEC in a CEABAC 10 Crohn's disease model (Sivignon 2015).

Thiazolylmannosides (TazMans) that have strong antiadhesive properties for *E. coli* strains implied in the gut inflammation of patients with Crohn's disease (Brument et al, 2013; Chalopin T et al, 2013 and 2015), Mydock-McGrane et al., 2016 disclosed in its Table 1 the generic structures of a number of alternative mannose-based FimH antagonists that have been published between 2005 and 2015.

All of them are encompassed.

ZFH-04269 as disclosed in Totsika M. et al, 2013 and all the compounds disclosed in Cusumano C K et al, 2011.

The FimH inhibitors disclosed in WO2013/134415 (VERTEX), WO 2014/055474 (VERTEX)

The FimH inhibitors disclosed in WO 2011/050323 (WASHINGTON UNIVERSITY), WO 2012/109263 (WASHINGTON UNIVERSITY), WO 2014/194270 (WASHINGTON UNIVERSITY), The FimH inhibitors disclosed in WO 2012/164074 (UNIVERSITAET BASEL) and WO 2011/073112 (UNIVERSITAET BASEL).

Other mannose derivatives have been proposed for treating AIECs based pathologies such as CD and UC. One of them is the compound of formula (I):

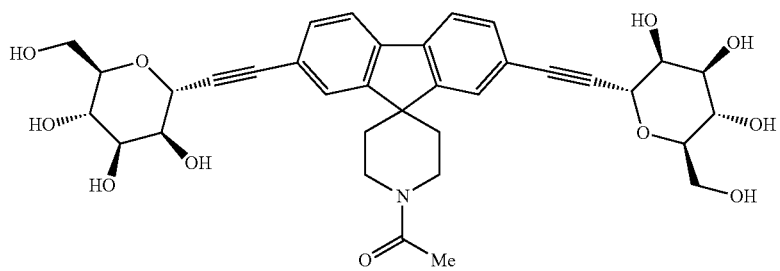 [SMILES: CC(=O)N1CCC2(CC1)c1cc(C#C[C@H]3O[C@H](CO)[C@@H](O)[C@H](O)[C@@H]3O)ccc1-c1ccc(C#C[C@H]3O[C@H](CO)[C@@H](O)[C@H](O)[C@@H]3O)cc12]

(1-(2,7-bis(((2R,3S,4R,5S,6R)-3,4,5-trihydroxy-6-(hydroxylmethyl)tetrahydro-2H-pyran-2-yl)ethynyl)spiro[fluorene-9,4'-piperidin]-1'-yl)ethan-1-one), which is currently clinically tested. It will be hereafter referred to as EB8018.

This compound comprises two mannoside residues held together by a chemically inert linker. These mannosides efficiently compete for binding with mannose residues such as those found on glycosylated proteins. Furthermore, because of its "bi-valent" nature, this compound can bind a FimH receptor on one bacterial cell, and another FimH on a different bacterial cell at the same time resulting in the enchaining of several bacterial cells together (Moor et al., 2017). This leads to the "clumping" of the bacteria, which has been shown to facilitate the selective clearing of bacteria from the gut lumen (Spaulding et al., 2017). In addition to facilitating clearance, the clumping process may significantly slow or prevent the penetration of FimH expressing bacteria into the mucus layer and the intestinal epithelium thereby preventing interaction with receptors such as TLR4, CEACAM6 and GP2, that contribute to the inflammation in the gut of patients with Crohn's disease.

Non-mannoside compounds have been also disclosed as potent FimH antagonists. They are for example disclosed in WO 2016/183501 (WASHINGTON UNIVERSITY) and WO 2014/173904 (VLAAMS INTERUNIVERSITAIR INSTITUUT VOOR BIOTECHNOLOGIE VZW). They are also encompassed in the present application.

By blocking the interaction of the FimH lectin of the FimH-expressing proteobacteria with the epithelial cells, the above-mentioned compounds inhibit their adhesion to the epithelial cells of the digestive and/or urinary tract mucosa and their subsequent invasion of both the ileum and the colon.

In another aspect, the present invention therefore relates to an in vitro method for predicting if a subject will benefit from a treatment with a FimH blocker, said method comprising the steps of the method disclosed previously, namely:
  a) isolating the nucleotide fraction of a biological sample from said subject,
  b) detecting the expression of the fimH gene in said nucleotide fraction by qPCR.

As shown in the experimental part below, step b) of said method is preferably performed by detecting the abundance of the fimH gene, and/or by detecting in the DNA of said sample the switch of the fim operon transcription from OFF to ON by any of the methods disclosed above. Said biological sample is preferably a stool sample.

All the embodiments described above for the detecting method of the invention apply mutatis mutandis to the predicting method of the invention.

In a preferred embodiment, the invention relates to an in vitro method for predicting a therapeutic response to a FimH blocker in a subject, said method comprising the steps of:
  a) isolating the nucleotide fraction of a stool sample from said subject,
  b) detecting the expression of the fimH gene in said nucleotide fraction by measuring the switch of the fim operon transcription from OFF to ON in said nucleotide fraction by qPCR,
  c) predicting that said subject will benefit from a treatment with a FimH blocker if the amplification of the ON position is superior to a reference value, as explained above.

In another preferred embodiment, the invention relates to an in vitro method for predicting a therapeutic response to a FimH blocker in a subject, said method comprising the steps of:
  a) isolating the nucleotide fraction of a stool sample from said subject,
  b) detecting the expression of the fimH gene in said nucleotide fraction by measuring the abundance of the fimH gene in said nucleotide fraction by qPCR,
  c) predicting that said subject will benefit from a treatment with a FimH blocker if the abundance of the fimH gene in said nucleotide fraction is superior to a reference value, as explained above.

All the embodiments and definitions disclosed above for the detecting method of the invention apply to this predicting method.

In a more preferred embodiment, said step b) consists in measuring the normalized amplification level of the ON position or the ON/OFF ratio or the ON/(OFF+ON) ratio of the fim operon transcription in said stool sample, and comparing same with a reference value, said reference value being preferably obtained by measuring the switch of the fim operon transcription from OFF to ON in the stool of healthy subjects.

In a more preferred embodiment, said step b) consists in measuring both the normalized amplification level of the ON position and the abundance of the fimH gene in said stool sample, calculating the ratio "ON/fimH" as explained above, and comparing same with a reference value, said reference value being preferably obtained after measuring the switch of the fim operon transcription from OFF to ON and the fimH abundance in the stool of healthy subjects.

In other terms, the molecular signature of the invention enables to identify sub-groups of patients that are either unresponsive or sensitive to FimH blocker treatment.

In another aspect, the present invention therefore relates to an in vitro screening method for identifying subsets of patients that are sensitive or unresponsive to a treatment with a FimH blocker, said method comprising the steps of the detecting method of the invention.

If the normalized amplification level of ON or the ON/OFF ratio or the ON/(OFF+ON) ratio of the fim operon measured in the stool sample of said subject is superior to said reference value, then said subject will be identified as being sensitive to a treatment with a FimH blocker. On the contrary, if the normalized amplification level of ON or the ON/OFF ratio or the ON/(ON+OFF) ratio of the fim operon measured in the stool sample of said subject is inferior to said reference value, then said subject will be identified as being sensitive to a treatment with a FimH blocker.

If the abundance of the fimH gene measured by using the appropriate pairs of primers is superior to a reference value, then it can be concluded that the tested subject hosts a high amount of FimH expressing bacteria in his gut, and will therefore be sensitive to a FimH blocker.

If the ratio FimS ON/FimH is superior to the reference value, then it can be concluded that the tested subject hosts a high amount of FimH expressing bacteria in his gut, and will therefore be sensitive to a FimH blocker. All the embodiments and definitions disclosed for the detecting method of the invention apply to this screening method.

The molecular signature of the invention can be used to adjust the dosage regimen of such a FimH blocker and to design tailored treatments for particular subsets of patients hosting high amount of FimH expressing proteobacteria. The detecting method of the invention indeed reveals, without any colonoscopy or biopsy analysis, if a patient hosts a low or high amount of FimH expressing proteobacteria in his/her gut. This information can be used to personalize his/her treatment based on this information by prescreening the stool samples of the patients for detecting the molecular signature of the invention before administering the FimH blocker.

In another aspect, the present invention relates to a method for treating subjects suffering from a disease caused by FimH proteobacteria, said method comprising the steps of:
- a) isolating the nucleotide fraction of a biological sample, for example a stool sample, from said subject,
- b) detecting the expression of the fimH gene in said nucleotide fraction by qPCR, preferably by measuring the switch of the fim operon transcription from OFF to ON in said nucleotide fraction by qPCR,
- c) administering a FimH blocker only in subjects hosting high amounts of FimH expressing proteobacteria in their gut Said subjects are preferably those in which the normalized amplification level of ON or the ON/OFF ratio or the ON/(ON+OFF) ratio of the fim operon is superior to a reference value, or those in which the abundance of the fimH gene measured by using the appropriate pairs of primers is superior to a reference value, or those in which the ratio FimS ON/FimH is superior to the reference value.

In this case, the present invention relates to a FimH blocker for use for treating subjects hosting high amounts of FimH expressing proteobacteria in their gut, preferably those in which the normalized amplification level of ON or the ON/OFF ratio or the ON/(ON+OFF) ratio of the fim operon is superior to a reference value, or those in which the abundance of the fimH gene measured by using the appropriate pairs of primers is superior to a reference value, or those in which the ratio FimS ON/FimH is superior to the reference value.

If the normalized amplification level of ON or the ON/OFF ratio or the ON/(ON+OFF) ratio of the fim operon or the fimH gene abundance or the FimS ON/FimH ratio measured in the sample of said subject is inferior to the respective reference value then administering a FimH blocker to said subject will be useless. In this case, other treatments have to be administered.

Other IBD treatments are for example chosen in the group consisting of: azathioprine, mesalamine, abatacept, adalimumab, anakinra, certolizumab, etanercept, golimumab, infliximab, rituximab, tocilizumab, natalizumab, corticosteroids, cyclosporine, methotrexate, tacrolimus, Anti-JAK (tofacitinib), anti-integrins (Vedolizumab, rhuMAb Beta7, MAdCAM-1 Antagonist), or Anti IL12/IL23 (Ustekinumab, ABT874).

All the embodiments and definitions disclosed for the detecting method of the invention apply to this treating method. A preferred biological sample is a stool sample.

In other terms, the invention relates to the use of a FimH blocker for preparing a drug intended to treat a subset of subjects that are sensitive to said treatment, i.e., in which FimH-expressing proteobacteria are detected according to the detecting method of the invention (for example, if the ON/OFF ratio or the ON/(ON+OFF) ratio or the fimH gene abundance or the ON/FimH ratio measured in the stool sample of said subjects is superior to the reference value). The FimH blocker can be used for treating a subset of subjects suffering from a disease caused by FimH proteobacteria that are sensitive to said treatment, i.e., in which FimH-expressing proteobacteria are detected according to the detecting method of the invention (for example, if the ON/OFF ratio or the ON/(ON+OFF) ratio of the fim operon or the fimH gene abundance or the ON/FimH ratio measured in the stool sample of said subjects is superior to the reference value). The subjects are preferably mammals and human beings that suffer from urinary tract infections (such as chronic cystitis), or an IBD (preferably Crohn's disease), these diseases being known to be caused—at least partially—by virulent FimH-expressing proteobacteria (Totsika et al, 2013; Mydock-McGrane et al, 2016).

All the embodiments and definitions disclosed for the detecting method of the invention apply to these treating methods.

Another interesting aspect of the molecular signature of the invention is to predict the potential virulence of proteobacteria present in stool samples of subjects. Based on this information, it is possible to diagnose diseases whose etiology involves virulent FimH-expressing proteobacteria and to monitor the activity of these diseases.

Diseases whose etiology involves virulent FimH-expressing proteobacteria are for example: urinary infections such as chronic cystitis and IBD (such as UC or CD, in adults or in children). These diseases will be herein referred to as "FimH proteobacteria related diseases". It also encompasses postoperative recurrence of Crohn's disease in patients that have been surgically treated.

In another aspect, the present invention relates to an in vitro method for diagnosing a FimH proteobacteria related disease in a subject, by detecting the presence of FimH expressing bacteria in a stool sample of a subject by means of the detecting method of the invention which is exposed above.

In another aspect, the present invention relates to an in vitro method for monitoring the evolution of a FimH proteobacteria related disease in a subject, by detecting the presence of FimH expressing bacteria in a stool sample of a subject by means of the detecting method of the invention which is exposed above.

If the normalized amplification level of ON or the ON/OFF ratio or the ON/(ON+OFF) ratio of the fim operon measured in the stool sample of said subject is superior to said reference value, then said subject will be diagnosed as suffering from a FimH proteobacteria related disease which is in a virulent state. On the contrary, if the normalized amplification level of ON or the ON/OFF ratio or the ON/(ON+OFF) ratio of the fim operon measured in the stool sample of said subject is inferior to said reference value, then said subject will be identified as healthy or at least not hosting FimH-expressing proteobacteria in its gut, therefore not likely to suffer from a FimH proteobacteria related disease such as IBD.

If the abundance of the fimH gene measured by using the appropriate pairs of primers is superior to a reference value, then it can be concluded that the tested subject will be diagnosed as suffering from a FimH proteobacteria related disease which is in a virulent state.

If the ratio FimS ON/FimH is superior to the reference value, then it can be concluded that the tested subject will be diagnosed as suffering from a FimH proteobacteria related disease which is in a virulent state. These results have been confirmed by the present inventors experimentally (see example 7 and FIG. 10).

In another aspect, the present invention relates to an in vitro method for testing the therapeutic efficiency of a treatment in a subject suffering from a FimH proteobacteria related disease, said method comprising the step of predicting the therapeutic response as described previously before and after the administration of said treatment.

It can be concluded that said treatment is efficient in said subject if the normalized amplification level of ON or the ON/OFF ratio or the ON/(ON+OFF) ratio of the fim operon or the fimH gene abundance, or the ON/FimH ratio measured in the sample obtained before said treatment is superior respectively to the normalized amplification level of ON or the ON/OFF ratio or the ON/(ON+OFF) ratio of the fim operon or the fimH gene abundance, or the ON/FimH ratio measured in the sample obtained after said treatment.

The efficiency of any treatment (even classical antibiotics) can be assessed by means of this method. In a preferred embodiment, said treatment is one of the FimH blocker disclosed above. All the embodiments and definitions disclosed for the detecting method of the invention apply to these methods.

In particular, it will be possible to use primers specifically amplifying specific regions within the FimS, the FimA and FimE region having the SEQ ID NO:15 to 20 or homologous regions thereof, preferably the regions having the SEQ ID NO: 21-33 by using the primer systems mentioned above. In another aspect, the present invention relates to nucleotide primers amplifying specifically the nucleotide regions within the FimS, the FimA and FimE regions having the SEQ ID NO:15 to 20 or the regions having the SEQ ID NO:21-33. It also relates to kits containing said primers.

These nucleotide primers have preferably at least 80%, preferably at least 90% or at least 95% identity with at least one fragment of the complementary sequence of SEQ ID NO:15 to 33.

More precisely, the present invention relates to kits containing at least one of the following primer pairs, that can be used to measure the amplification level of the ON position of the fim operon:
[SEQ ID NO:1; SEQ ID NO:3],
[SEQ ID NO:2; SEQ ID NO:4],
[SEQ ID NO:5; SEQ ID NO:7],
[SEQ ID NO:6; SEQ ID NO:8].

Furthermore, said kits may contain at least one of the following primer pairs, that can be used to measure the amplification level of the OFF position of the fim operon:
[SEQ ID NO:1; SEQ ID NO:2],
[SEQ ID NO:3; SEQ ID NO:4],
[SEQ ID NO:5; SEQ ID NO:8],
[SEQ ID NO:7; SEQ ID NO:8].

Furthermore, said kits may contain at least one of the following primer pairs, that can be used to measure the abundance of the fimH gene:
[SEQ ID NO:35; SEQ ID NO:36],
[SEQ ID NO:37; SEQ ID NO:38],
[SEQ ID NO:39; SEQ ID NO:40].

Preferably, the kits contain at least the primer pairs [SEQ ID NO:5; SEQ ID NO:7] and [SEQ ID NO:6; SEQ ID NO:8]. More preferably, the kits contain the primer pair [SEQ ID NO:5; SEQ ID NO:7]. More preferably, the kits contain at least the primer pair [SEQ ID NO:35; SEQ ID NO:36], optionally in combination with the primer pair [SEQ ID NO:5; SEQ ID NO:7].

The invention also concerns the nucleotide primers per se, having the following sequence: SEQ ID NO: 1 (p1), SEQ ID NO:2 (p2), SEQ ID NO: 3 (p3), SEQ ID NO:4 (p4), SEQ ID NO: Z5 (p5), SEQ ID NO:6 (p6), SEQ ID NO: 7 (p7), SEQ ID NO:8 (p8), SEQ ID NO:35, SEQ ID NO:36.

In a preferred embodiment, the primers of SEQ ID NO:1 to 8 and/or SEQ ID NO:35 to 40 can be used to screen the samples before implementing any of the methods of the invention.

In another aspect, the present invention relates to the pairs of primers p1-p8 of SEQ ID NO:1 to 8 identified by the inventors as reproducible and reliable tools for measuring the amplification level of the ON position or the ON/OFF ratio or the ON/(ON+OFF) ratio of the fim operon in stool samples. It also relates to kits containing said pairs of primers. Any appropriate combination between the said primers for detecting the OFF and ON position of the fim operon is herewith encompassed.

In another aspect, the present invention relates to the pairs of primers of SEQ ID NO:35 to 40 identified by the inventors as reproducible and reliable tools for measuring the abundance of the fimH gene in stool samples. It also relates to kits containing said pairs of primers. Any appropriate combination between the said primers and those for detecting the OFF and ON position of the fim operon is herewith encompassed.

Moreover, the invention relates to a kit (or micro-array) containing (or carrying) probes targeting at least one of the following nucleotide regions:

```
SEQ ID NO: 9 (the small characters
representing known polymorphisms):
TTAACTaATTGATAATAAAGTTAAAAAACAAATAAATACAAGACAATTGG GGCCAAACTGTCtATATCATAAATAAGTTACGTATTTTTTCTCAAGCA SEQ ID NO: 10 (the small characters
representing known polymorphisms):
AGTCAAACTCGTTGACAAAACAAAGTGTACAGAACGACTGCCCATGTCGA TTTAGAAATAgTTTTTTTAAAGGAAAGCAGCATGAAA
```

SEQ ID NO:9 and SEQ ID NO:10 correspond to the switch region of the fimS gene. Probes hybridizing these nucleotide regions may therefore be useful for detecting the ON position of the fim operon.

In a preferred embodiment, the probes of the invention hybridize the IRR (Inverted Repeat Region) located in the FimS gene, having SEQ ID NO:11 and/or SEQ ID NO:12.

In one embodiment, the invention relates to probes hybridizing specifically the nucleotide regions of SEQ ID NO:9, SEQ ID NO:10, SEQ ID NO:11 and/or SEQ ID NO:12.

In another embodiment, the invention relates to probes hybridizing specifically the nucleotide regions of the fimH gene of SEQ ID NO:34, especially the probes of SEQ ID NO:41, SEQ ID NO:42 and SEQ ID NO:43.

Specific hybridization is preferably observed under high stringency conditions, i.e., when the temperature and ionic strength conditions are chosen so as to allow the hybridization between two complementary DNA fragments to be maintained. By way of illustration, high stringency conditions can be as follows. The DNA-DNA or DNA-RNA hybridization is carried out in two steps: (1) prehybridization at 42° C. for 3 hours in phosphate buffer (20 mM, pH 7.5) containing 5*SSC (1*SSC corresponds to a 0.15 M NaCl+ 0.015 M sodium citrate solution), 50% of formamide, 7% of sodium dodecyl sulfate (SDS), 10*Denhardt's, 5% of dextran sulfate and 1% of salmon sperm DNA; (2) actual hybridization for 20 hours at a temperature dependent on the size of the probe (i.e. 42° C. for a probe of size>100 nucleotides), followed by two 20-minute washes at 20° C. in 2*SSC+2% SDS and one 20-minute wash at 20° C. in 0.1*SSC+0.1% SDS. The final wash is carried out in 0.1*SSC+0.1% SDS for 30 minutes at 60° C. for a probe of size>100 nucleotides. The high stringency hybridization conditions described above for a polynucleotide of defined size will be adjusted by those skilled in the art for oligonucleotides of greater or smaller size, as well-known in the art.

The invention also relates to nucleic microarray carrying said probes t. According to the invention, a "nucleic microarray" consists of different nucleic acid probes that are attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes can be nucleic acids such as cDNAs ("cDNA microarray") or oligonucleotides ("oligonucleotide microarray"), and the oligonucleotides may be about 25 to about 60 base pairs or less in length. Said nucleic acid microarray may comprise additional nucleic acids specific for additional genes and optionally one or more reference gene(s), but preferably consists of a maximum of 500, 400, 300, 200 preferably 100, 90, 80, 70 more preferably 60, 50, 45, 40, 35, 30, 25, 20, 15, 10, or even less (for instance 9, 8, 7, 6, 5, 4, 3, 2 or 1) distinct nucleic acids.

Said kits (or microarrays) may comprise additional reagents (e.g., primers, probes or antibodies) that are specific for additional genes or gene products of one or more reference gene(s). Reference genes herein designate genes having a ubiquitous level of expression and/or abundance across bacteria, that can be used to normalize the gene levels for the signature. Said kit may also contain instructions for how to use the kit in order to reduce the methods of the invention to practice.

The present inventors propose to use these kits, primers, and/or probes (or the microarrays carrying the said probes) for detecting the presence of FimH-positive expressing proteobacteria in a stool sample of a subject or for predicting if a subject will benefit from a treatment with a FimH blocker or for testing the therapeutic efficiency of a treatment in a subject suffering from a FimH proteobacteria related disease. It is also possible to use these kits or microarrays in the treating, diagnosing and monitoring methods disclosed above.

EXAMPLES

Figure 1:
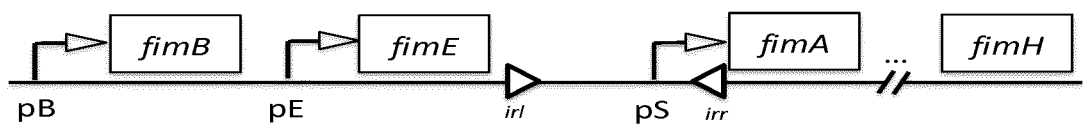
FIG. 1 discloses the structure of the fim operon, in position ON or in position OFF (from Van der Woude and Baumler, 2004).
Figure 1:
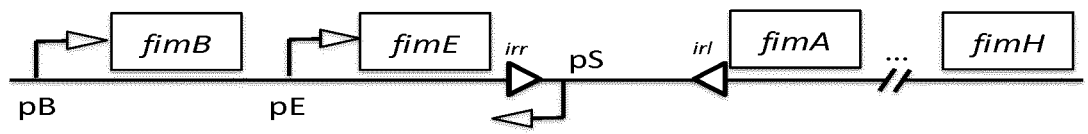

1. Description of the qPCR Assay of the Invention

The inventors have developed a qPCR assay based on the FimH switch mechanism to be used as a complementary diagnostic.

Aggregation tests have been performed initially on all available isolated strains and later in more complex samples such biopsy samples of CD patients which can contain a mixture of bacterial strains. Sequencing data was used to determine the FimS position in the isolated strains, whilst FimS qPCR assay has been performed on DNA extracted from the stool samples of CD patients. Ultimately for the qPCR test to be useful as a diagnostic test, the assay performed on the DNA extracted from stool samples has to correlate to the aggregation tests performed on the patient's mucosal biopsy.

The following tests have been carried out:
1. the link between FimS switch mechanism and aggregation to EB8018 experimentally has been confirmed,
2. a qPCR based assay FimS switch mechanism assessing the FimS switch mechanism in stool samples has been developed, The performance of this qPCR assay in the stool of CD patients in terms of correlation with ileal E. coli aggregation to EB8018 is evaluated.

1.1. Material and methods
1. Stool Collection & DNA Extraction

An exploratory longitudinal study of CD patients—CrohnOmeter (Enterome sponsored)—was conducted between July 2012 and December 2014, at the St. Antoine and St. Louis Hospitals (Paris, France) and at the French patient association l'Association Frangois Aupetit (AFA, Paris, France). Eligibility of 98 subjects volunteering for participation in this study was assessed. Inclusion criteria were age ≥18 years, an established diagnosis of CD according to endoscopic, radiological and/or histological features. The main exclusion criteria were the use of antibiotics in the last 8 weeks preceding inclusion, history of intestinal resection, and bowel cleaning for colonoscopy in the last 3 months preceding inclusion. Patients were followed longitudinally for about 9 months, providing monthly stool samples collected at home.

Stool samples were collected by CD patients at home using Sarstedt tubes (Numbrecht, Germany) filled with 9 ml of preservative buffer. Upon reception, the tubes were stored at −80° C. Aliquoting and DNA isolation were outsourced to Eurofins/GATC Biotech (Konstanz, Germany). Tubes have been aliquoted by batch and were stored at −80° C. until extraction. For isolation of bacterial content, a commercial extraction kit, the QIAamp Stool DNA mini kit (Qiagen, Hilden, Germany) was used. DNA concentrations were measured using Qubit fluorometric quantitation (Life Technologies, Carlsbad, California, United States).

2. Strains Isolation and Culture

110 E. coli strains from La Girona University (Margarita Medina-Martinez Lab-Girona-Spain) and Cornell (Kenneth Simpson Lab—Ithaca—USA) have been made available through MTA. These isolated strains had been previously extracted from the stool or ileal/colonic biopsies of IBD patients or controls and had been characterised for their AIEC phenotype (for Cornell strains see Dogan B. et al., 2014; Baumgart M. et al., 2007, summarized in the Appendix). Those 110 strains have been sent to SMALTIS (Besangon, France) who is in charge of all laboratory work. An additional 3 non E. coli strains have been ordered as well as LF82 and LF82 deltaFimH that serve as respectively positive and negative controls.

Three days before aggregation assays, bacterial strains were defrosted on TSA (Tryptone Soya Agar) plates. A first overnight culture was performed by inoculation of 3 mL of LB broth with a single colony of bacteria followed by a second overnight culture (1 mL of the first culture+4 mL LB broth).

3. Aggregation Test

A grey zone contained all remaining strains (hence with low aggregation)

This protocol was applied to the 113 isolated bacterial strains. On each plate, a positive control (LF82) and a negative control (LF82-ΔFimH) were used.

4. Extraction of DNA from Isolated Strains, Sequencing and Bioinformatics

DNA extraction were performed by SMALTIS using the ZymoBIOMICS DNA PrepKit according to manufacturer's instructions. The genome sequencing was performed by GATC (Konstance, Germany) and was carried out as 300 bp paired end with a MiSeq, using the V4 chemistry from Illumina, which will not vary for the duration of this project Structure of EB8018

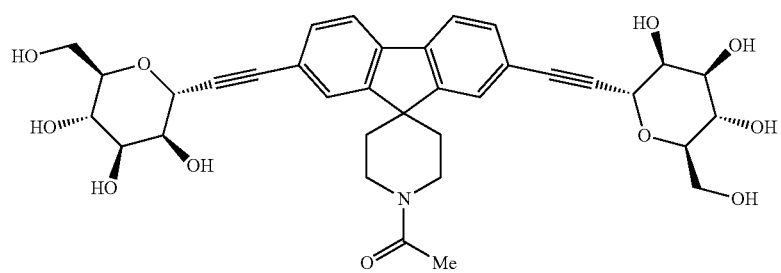 [SMILES: CC(=O)N1CCC2(CC1)c1cc(C#C[C@H]3O[C@H](CO)[C@@H](O)[C@H](O)[C@@H]3O)ccc1-c1ccc(C#C[C@H]3O[C@H](CO)[C@@H](O)[C@H](O)[C@@H]3O)cc12]

Six concentrations of EB8018 (sample SP-0010269-017 produced by China Gateway) were tested in the aggregation assays (1 nM/10 nM/100 nM/1 μM/10 μM and 100 μM), 500× working solutions were prepared in pure DMSO by 10-fold serial dilutions from a 100 mM stock solution (65 mg EB8018+1 mL DMSO; $M_{EB8018}$:649.68 g/mol). The 500× working solutions (1 μM, 10 μM, 100 μM, 1 mM, 10 mM and 100 mM) were split into aliquots and stored at −20° C., until use.

On the day of the test, an aliquot of each EB8018 500× working solution (1 μM, 10 μM, 100 μM, 1 mM, 10 mM and 100 mM) was defrosted and diluted twice in LB medium (1:20 for the first dilution and 1:25 for the second dilution) to obtain respectively six 2× working solutions (2 nM, 20 nM, 200 nM, 2 μM, 20 μM and 200 μM). The second overnight bacterial cultures were diluted in LB medium (50-fold dilution). Fifty μL of these bacteria dilutions were dispensed into 96-well plates (8 wells/strain). Fifty μL of the EB8018 2× working solutions or fresh LB or LB with 0.2% DMSO were added to the wells. Microplates were incubated for 5 hours at 37° C. under constant shaking (200 rpm). Every hour, each well was observed and the starting time of aggregation was recorded. After 5 hours of incubation, a picture was taken only in wells where an aggregation was observed. For each concentration and each time point, aggregation was evaluated by a technician. The level of aggregation was reported according to four different levels as follows:

"−" for no aggregation
"+/−−" for low aggregation
"+/−" for moderate aggregation
"+" for strong aggregation For further statistical analysis, the aggregation to EB8018 by strains was determined using the following rule:
An isolated strain did aggregate if at least one "+" or one "+/−" across all conditions (concentration and time of incubation)
An isolated strain did not aggregate if all results were negative ("−") across all conditions (concentration and time of incubation)

to ensure continuity. Negative controls are added to each of the sequencing runs and a final pared score analysis took place to ensure a suitable quality level. To control the sequencing process for contaminations, we used a PhiX control.

The E. coli strain 'LF82' was used as reference for the mapping. This strain contains 4376 genes and the sequence was uploaded from NCBI. Alignment of the LF82 genes with all isolated E. coli genomes was done using these following criteria: 95% of identity and 90% of coverage. A table of the genes presence and absence in each isolated genome has been generated.

5. qPCR Design

Figure 3:
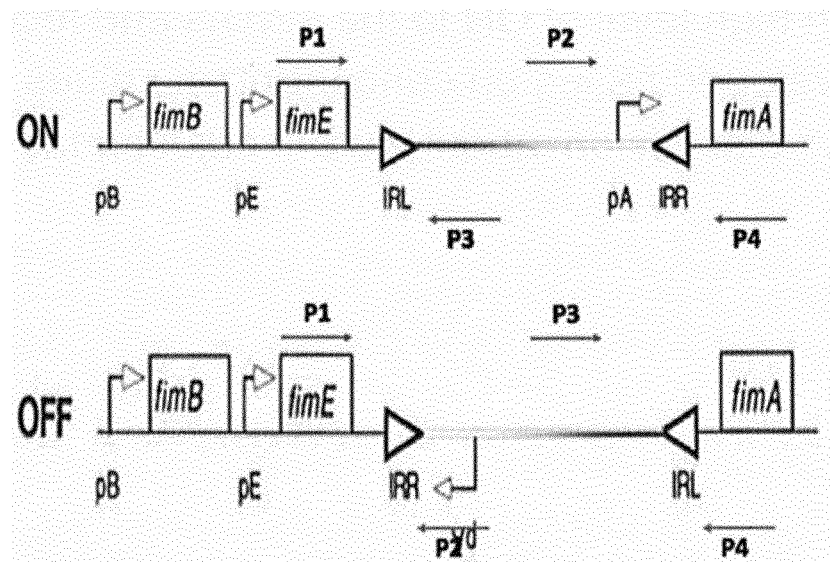
FIG. 3 discloses the position of the two different sets of primers used in the present invention (p1-p4 in A, p5-p8 in B).
Figure 3:
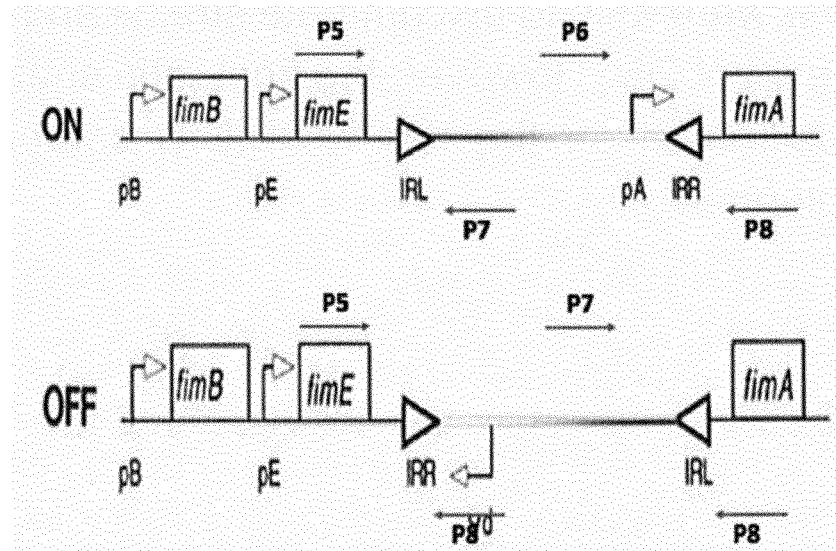

The regions of the fimE, fimS and fimA genes were selected from the Escherichia coli LF82 genome from Ensembl Bacteria database. 391 metagenomics CD samples available in the inventors internal database were mapped on the fimE/fimS/fimA region to inspect coverage and polymorphisms and select the candidate regions for qPCR primers. A 4 primers strategy was developed, where 2 primers are designed on the fimS region (on the forward and reverse strand) while the others 2 are designed on the fimE (forward strand) and fimA (reverse strand) regions, as shown in FIG. 3.

TABLE 1

| Name of the primer | Sequence of the primer | SEQ ID NO: |
|---|---|---|
| p1 | GTAATGCTGCTCGTTTTGCC | SEQ ID NO: 1 |
| p2 | CATATAGCGGAGGTGATGTGAA | SEQ ID NO: 2 |
| p3 | TGCGCGATGCTTTCCTCTAT | SEQ ID NO: 3 |
| p4 | GCGCAAGCGGCGTTA | SEQ ID NO: 4 |
| p5 | CGGATTATGGGAAAGAAAT | SEQ ID NO: 5 |
| p6 | TCAAACAGTTAGATGCTTT | SEQ ID NO: 6 |

TABLE 1-continued

| Name of the primer | Sequence of the primer | SEQ ID NO: |
|---|---|---|
| p7 | CGATGCTTTCCTCTATGA | SEQ ID NO: 7 |
| p8 | TTGTTTTGTCAACGAGTT | SEQ ID NO: 8 |

Table 1 above recapitulates the nucleotide sequences of the 8 tested primers.

Four separate qPCR reactions can be performed on each sample, involving the combinations of primers p1+p3 (SEQ ID NO:1 and 3) and p2+p4 (SEQ ID NO:2 and 4) to detect the ON switch and p1+p2 (SEQ ID NO:1 and 2) and p3+p4 (SEQ ID NO:3 and 4) to detect the OFF switch.

Eight assays have been designed and applied to the following samples: 5 DNAs extracted from the stool of CD patients selected on their NGS sequence information on the FimS region. The two samples with the highest reads in the ON position were selected and two samples with no reads in the ON position and maximum sequencing depth and an intermediate sample.

A SYBR based assay has been validated, targeting the FimS on/off switch. The two assay sets were called p1-4 and p5-p8, and differ in Tm: 60° C. for set p1-p4 and 55° C. for set p5-p8. Of the eight assays designed, four target the FimS OFF switch (p1p2, p3p4, p5p6, p7p8) and four target the ON switch (p1p3, p2p4, p5p7, p6p8).

TABLE 2

Expected size for the assays targeting the FimS switch

| Assays | Region | Expected size |
|---|---|---|
| p1p2 | FimS-OFF | 268 |
| p3p4 | FimS-OFF | 293 |
| p1p3 | FimS-ON | 162 |
| p2p4 | FimS-ON | 403 |
| p5p6 | FimS-OFF | 198 |
| p7p8 | FimS-OFF | 95 |
| p5p7 | FimS-ON | 139 |
| p6p8 | FimS-ON | 154 |

6. qPCR Protocols

DNA was diluted 20 times in DNase/RNase free distilled water prior to analysis. The qPCR analysis was performed on 4 CD samples with the 8 assays (SYBR-based) in duplicate 10 µl reactions on the LC480 (Roche) instrument, using TATAA SYBR® GrandMaster Mix (TATAA Biocenter AB). 2 µl of the diluted sample were added to the reactions. EpMotion 5070 (Eppendorf) robot performed all the pipetting. TATAA interplate calibrator (IPC) and NTCs were included on all plates. All the samples were run in the same plate with 4 assays/run (due to different Tm between the 2 set of primers). The following protocol and conditions were used for the qPCR analysis.

Master Mix Protocol:

| Type | Comment | Stock Conc (µM) | FINAL Conc. (nM) | 1 rxn 1 |
|---|---|---|---|---|
| Primer pair: | (Fw + Rv) | 10 | 400 | 0.4 |
| MMX: | TATAA SYBR GrandMaster | r2x | — | 5 |
| H2O: | | | | 2.6 |
| Sum: | | | | 8 |

Temperature Protocol:

| Program | Temp (° C.): | Time (s): | Cycles: | Fluorescence acquisition |
|---|---|---|---|---|
| Polymerase activation: | 95 | 60 | 1 | |
| Amplification: | | | | |
| Denaturation | 95 | 5 | | |
| Annealing | 60/55 | 30 | 45 | |
| Extension | 72 | 10 | | SYBR |
| Dissociation curve: | | | | |
| Denaturation | 95 | 15 | | |
| Melting | 60/55 | 15 | 1 | |
| | 95 | — | | Continious (SYBR) |

Cq-values were retrieved by absolute quantification/2nd derivative max for all samples in the Light Cycler 480 (Roche) software.

I.II. Results

Association between the ON switch and aggregation of the bacteria to EB80018 in isolated strains The aggregation tests on EB8018 on the 110 isolated *E. coli* strains together with three additional non *E. coli* strains has led to the following conclusion.

Aggregation assays were successfully performed for the series of 110 strains. Positive control LF82 aggregated from 2 h of incubation. After 5 h of incubation, a strong aggregation was observed for concentrations 1 nM, 10 nM and 100 nM. At concentration of 1 µM, a moderate aggregation was observed. Negative control LF82-ΔFimH did not aggregate with EB8018 whatever the concentration tested and whatever the time of incubation. The experiment highlighted a wide heterogeneity of aggregation profiles among *E. coli* isolates. Some of them aggregated very quickly and strongly, while others needed more time. For isolates with a slight aggregation, the phenomenon appeared stable over time. The heterogeneity of aggregation profiles could be attributed to the size of bacteria (microscopic observations revealed a morphological heterogeneity among the collection) and/or to the structure/function of FimH protein.

For each isolated strain, aggregation to EB8018 was measured at 6 different concentrations of EB8018 every hour for 5 hours with 4 different levels as described before. The aggregation to EB8018 was categorized in three groups 'aggregation', 'no aggregation' and 'grey zone' (see above). Among all analyzable strains, 42% did aggregate, 44% did not aggregate and 13% were classified on the grey zone (low aggregation).

Association tests were performed between aggregation classification and some phenotype/information. There were no association between aggregation and the AIEC phenotype (p-value=0.15, Pearson's Chi-squared test).

The number of reads that mapped to FimA and FimE on both ON and OFF positions was analyzed using the sequence data of those strains, and the percentage of reads on FimS was estimated as the mean of percentage of reads mapped to FimA ON and FimE ON. If no read mapped to FimA on position ON and OFF or no read mapped to FimE on position ON and OFF, the percentage of reads on FimS cannot be estimated.

Figure 2:
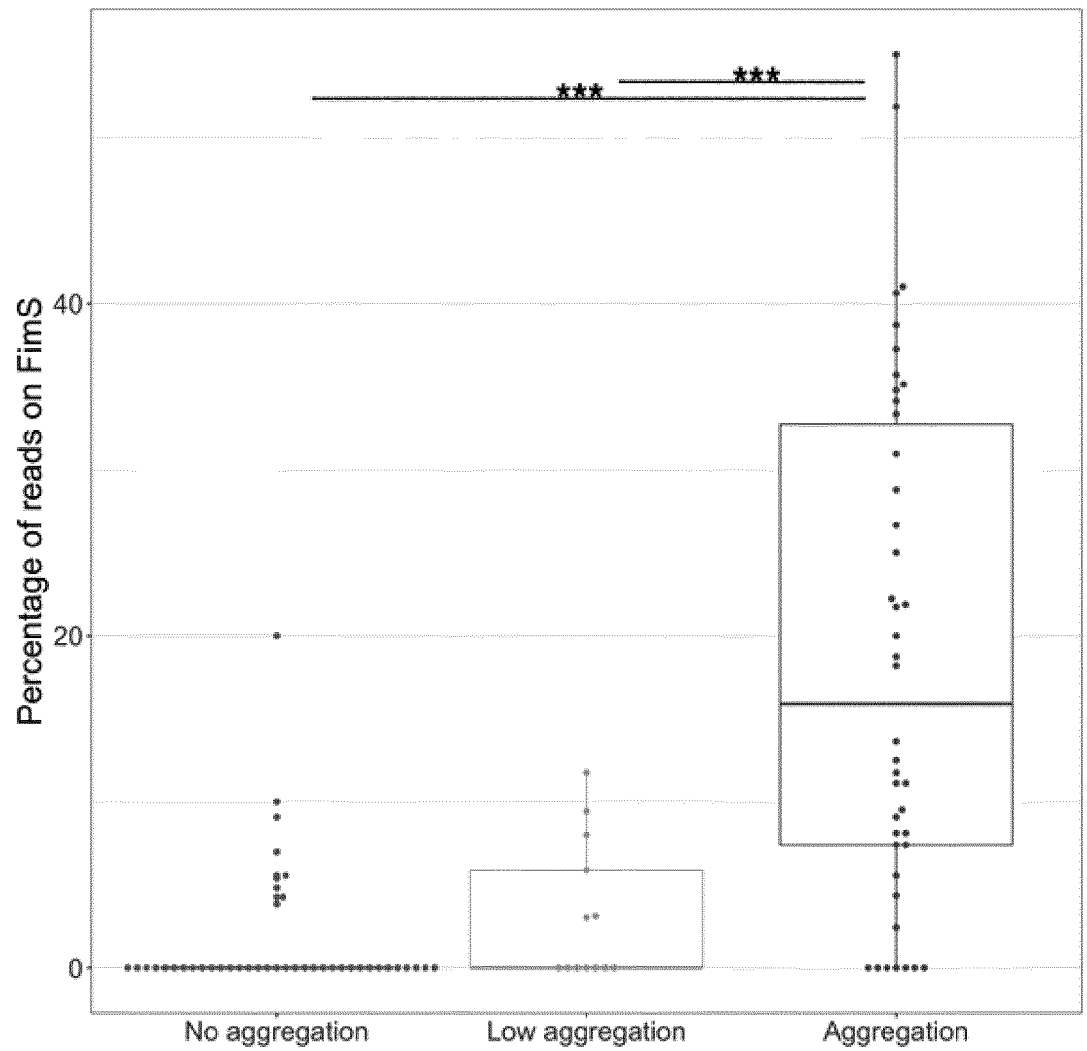
FIG. 2 discloses the percentage of ON reads measured on 113 aggregating or non-aggregation bacterial isolates.

The FIG. 2 shows the distribution of percentage of reads on FimS according to our aggregation classification. There was a huge association between the percentage of reads on FimS and the aggregation classification (p<0.0001, Wilcoxon rank test; Low aggregation (grey zone) vs. Aggregation, p<0.0001, Wilcoxon rank test).

A cutoff of 1% was applied on the percentage of reads on FimS. The confusion matrix below reports the FimS classification according to aggregation outcome. 35 strains had more than 1% of reads on FimS and did aggregate with EB8018 and 24 strains had less than 1% of reads on FimS and did not aggregate with EB8018. The number of false positive is 9 and the number of false negative is 7, hence the sensitivity reached 0.83 and the specificity reached 0.73. 13 strains were on the grey zone: 6 of them had more than 1% of reads on FimS and 7 of them had less than 1%. For 11 strains there was no reads on FimA or FimE so it was not possible to estimate the percentage of reads on FimS, however these strains did no aggregate with EB8018.

TABLE 3

Conclusion: FimS in ON position is characteristic of strains that aggregate to EB8018.

| | | Aggregation outcome | | | |
|---|---|---|---|---|---|
| | | Aggregation | Grey zone (agg = +/--) | No aggregation | |
| At least 1% read on FIMS | TRUE | 35 | 6 | 9 | 0.80 |
| | Unknown | 0 | 0 | 11 | — |
| | FALSE | 7 | 7 | 24 | 0.77 |
| | | 0.83 | — | 0.73 | |

Characterization of the qPCR Primers Specific of the Switch Change

The strong association between aggregation to EB8018 and FimS switch led to the development of qPCR assays targeting the ON position of FimS, the OFF position of FimS and the FimH region as reference.

A qPCR assay targeting the four regions identified above has been developed. Two sets of four assays were designed as shown on FIGS. 3 A and B where 4 primers (p2, p3, p6 and p7) were designed on the fimS region (on the forward and reverse strand) while two others were designed on the fimE (p1, p5, forward strand) and two others on the fimA (p4, p8, reverse strand) regions.

The designed assays were validated using a simplified validation protocol using 10 samples (5 strains and 5 fecal samples). Validation was based on a standard curve with 5 target concentrations measured in duplicates.

TABLE 4

Information for the ten samples used for the technical development of FimS qPCR assay

| ID | Other ID | Type | Origine | Tissue/Source | Disease | Aggregation? | Prediction of aggregation with FimS |
|---|---|---|---|---|---|---|---|
| 09_404_G | C08914 | Isolated strain | cornell | Stool | Control | Aggregation | ON |
| 38AW_1 | B96817 | Isolated strain | cornell | Intestinal Biopsy | ICD | Aggregation | ON |
| 538_6 | C08890 | Isolated strain | cornell | Intestinal Biopsy | ICD | Absence of aggregation | OFF |
| 40EM_1 | B96818 | Isolated strain | cornell | Intestinal Biopsy | UC | Absence of aggregation | OFF |
| 09_406_B | C08915 | Isolated strain | cornell | Stool | Control | Grey zone | OFF |
| AFA15_13 | S8 | stool sample | CrohnOmeter | Stool | CD | — | ON |
| AFA19_10 | S9 | stool sample | CrohnOmeter | Stool | CD | — | Grey |
| AFA38_06 | S6 | stool sample | CrohnOmeter | Stool | CD | — | OFF |
| AFA59_06 | S7 | stool sample | CrohnOmeter | Stool | CD | — | OFF |
| AFA70_03 | S10 | stool sample | CrohnOmeter | Stool | CD | — | ON |

SYBR based assays targeting the FimS on/off switch have been developed. As described on the material and methods section, two sets of four assays were developed; of the eight assays designed, four target the FimS OFF switch (p1p2, p3p4, p5p6, p7p8) and four target the ON switch (p1p3, p2p4, p5p7, p6p8). As first results, Enterome checked the correct amplification and the linearity of all PCR for all samples. An exploratory analysis was done to investigate a ratio between OFF and ON assays on unnormalized values (in Cq). Based on primary data, it was possible to discriminate strains and feces with high level of ON to the strains and feces with low level of ON. Thus, eight assays have been validated. The ON switch was detected by the four following assays: p1.p3; p2.p4; p5.p7; and p6.p8. The OFF switch was detected by the four following assays: p1.p2; p3.p4; p5.p8; and p7.p8.

After the technical development and validation, for each assay and each PCR product from the five stool samples, the efficiency of PCR reactions was estimated and one PCR product by assay was selected, maximizing the efficiency for further normalization. However, a good efficiency was observed for all assays (ranged from 0.90 to 0.98). Finally, efficiency, LOD and LOQ values as well as normalization parameter were saved for further normalization of new samples (see table 4 below for details).

TABLE 5

Normalization settings for the 8 Fims assays.

| Ids | Patients/PCR product | Assays | slope | intercept | efficiency | LOQ (Copies/rxn) | LOQ (Cq) | LOD (Copies/rxn) | IPC Efficiency plates |
|---|---|---|---|---|---|---|---|---|---|
| S10.AFA70_03.p1.p2 | AFA70_03 | p1.p2 | −3.44 | 33.85 | 0.95 | 20 | 29.58 | 3.440 | 14.31 |
| S7.AFA59_06.p1.p3 | AFA59_06 | p1.p3 | −3.37 | 34.33 | 0.98 | 20 | 30.3 | 5.438 | 14.31 |
| S9.AFA19_10.p2.p4 | AFA19_10 | p2.p4 | −3.58 | 35.23 | 0.9 | 200 | 27.15 | 4.003 | 14.31 |
| S10.AFA70_03.p3.p4 | AFA70_03 | p3.p4 | −3.51 | 34.93 | 0.93 | 20 | 30.61 | 5.932 | 14.31 |
| S10.AFA70_03.p5.p6 | AFA70_03 | p5.p6 | −3.37 | 34.03 | 0.98 | 20 | 29.4 | 4.328 | 14.40 |
| S6.AFA38_06.p5.p7 | AFA38_06 | p5.p7 | −3.39 | 34.44 | 0.97 | 20 | 29.98 | 7.893 | 14.40 |
| S7.AFA59_06.p6.p8 | AFA59_06 | p6.p8 | −3.57 | 35.64 | 0.91 | 200 | 27.67 | 5.281 | 14.40 |
| S10.AFA70_03.p7.p8 | AFA70_03 | p7.p8 | −3.51 | 36.08 | 0.93 | 20 | 31.26 | 8.760 | 14.40 |

The PCR products for all the primer pairs for a selection of 5 samples were sequenced by GATC using Sanger technology. The alignments showed no cross match against any unexpected bacteria. The inserts were also aligned on the *Escherichia coli* K12 reference genome to check their positions around the fimS region. The alignments of the inserts corresponded to the regions of amplification around the fimS region, and, as expected, the primers corresponding to the ON position were aligned on the reverse strand or are split between the forward and reverse strand when they overlap one of the two transposons.

For the development of a PCR assay based on the ratio between two assays (for example ratio or delta between ON and OFF targeted regions), care should be taken to selected the two assays with the highest efficiencies. PCR efficiency can be used to gauge the performance of PCR assays.

The PCR amplification efficiency values were estimated using the slope of standard curves. The variability of OFF targeted assays was lower than the variability for ON targeted assays. For all assays, the median of efficiency values was always lower than 1 (corresponding to 100%).

A linear regression line was plotted and the regression equation reported with the $r^2$ factor. The assays were designed to catch the same quantity of DNA and the same mechanism hence assays should be correlated to each other with a low variability and a slope of 1 with a intercept of 0.

A very good correlation was observed for p3.p4 and p7.p8 ($r^2=0.99$) and the slope was almost 1 (slope=0.972) with an intercept close to 0. Associations between p1.p2 and p3.p4 and between p1.p2 and p7.p8 were also good, even if the correlation coefficient was biased by an outlier. A high variability was observed for p5.p6.

A good correlation was observed for p1.p3 and p5.p7 the slope was not equal to 1 and a shift for the intercept was observed. This shift was induced by low concentrations. For other associations, the correlation was slower, except for p1.p3 and p6.p8 but for this comparison, the dispersion was larger for low Cq values.

Figure 4:
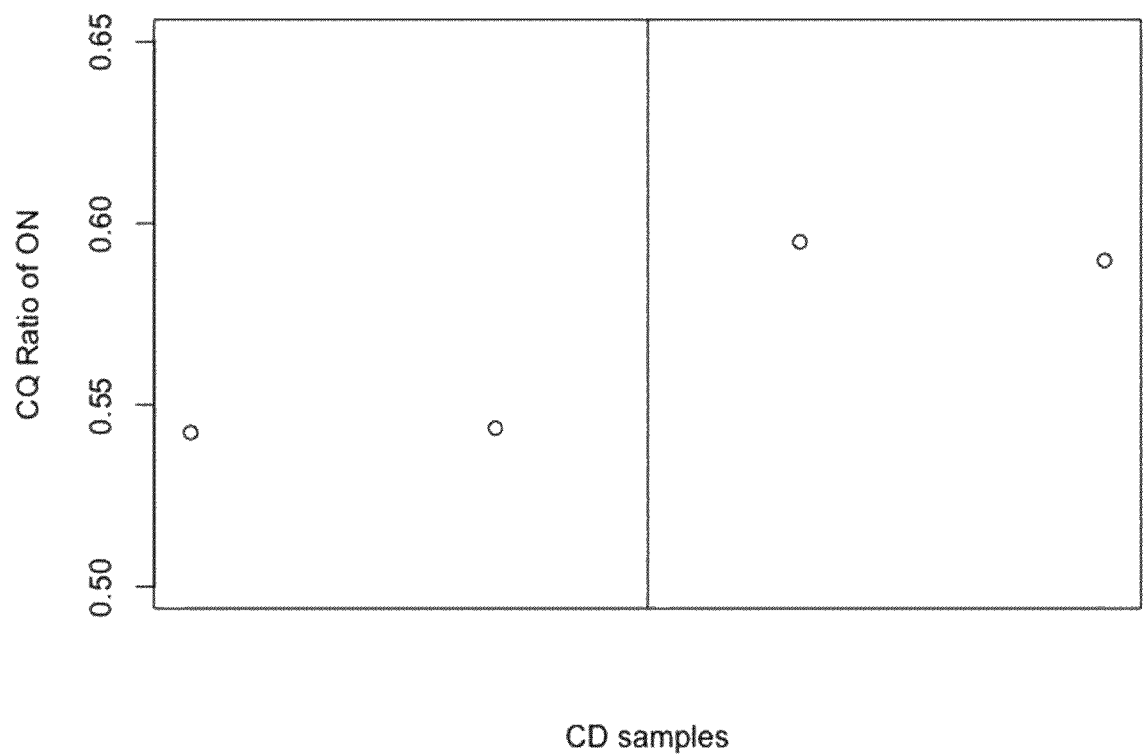
FIG. 4 discloses the ON/(OFF+ON) ratio measured in CD feces. The two samples on the left have a lower CQ ratio than the two samples on the right, indicating a higher amount of bacteria in the ON position.

As can be seen in FIG. 4, the two FimH "ON" samples are clearly separated from the two FimH "OFF" samples based on the qPCR assays. In particular when using the assays p1-p3 and p5-p7 to measure the ON expression and assays p3-p4 and p7-p8 to measure the OFF position, one can clearly see that a good cutoff would be between the values of 55 and 58% when calculated based on the Cq values.

II. Use of the qPCR Assay of the Invention on Two Different Representative Populations 1. MOBIDIC Study A clinical study for MOlecular BIomarkers and Adherent and Invasive *Escherichia coli* (AIEC) Detection study In Crohn's disease patients (MOBIDIC) was conducted between September 2016 and October 2017. Eligibility of 122 Crohn's disease patients in this multicenter study was assessed. Inclusion criteria were (i) male or female between 18 and 75 years of age, inclusive (ii) diagnosis of ileal or ileo-colonic Crohn's disease for a minimum of 3 months prior to inclusion (iii) an ileocolonoscopy scheduled prior to study inclusion (iv) agreeing to participate and to sign an informed consent form (v) able to perform stool collection at home. The main exclusion criteria were (i) colonic Crohn's disease of L2 phenotype based on Montreal classification (ii) extensive small bowel resection (>100 cm) or short bowel syndrome (iii) bowel strictures/stenosis contraindicating ileocolonoscopy (iv) currently with an ostomy or an ileoanal pouch (iv) currently receiving total parenteral nutrition (v) bowel preparation received in the previous 3 months (vi) an increased risk of hemorrhage (patients with anticoagulant/antiplatelet therapy) (vii) history of intestinal carcinoma or colorectal cancer, alcohol or substance abuse, chronic uncontrolled disorders.

2. Stool Sample Collection and DNA Extraction

Stool samples were collected by CD patients at home using Sarstedt tubes (Numbrecht, Germany) filled with 9 ml of a preservative buffer. Upon reception, the tubes were stored at −80° C. Aliquoting and DNA isolation were outsourced to Eurofins/GATC Biotech (Konstanz, Germany). Tubes have been aliquoted by batch and were stored at −80° C. until extraction. For isolation of bacterial content, a commercial extraction kit, the QIAamp Stool DNA mini kit (Qiagen, Hilden, Germany) was used. DNA concentrations were measured using Qubit fluorometric quantitation (Life Technologies, Carlsbad, California, United States).

3. Biopsies Collection

Mucosal specimens, isolated from CD patients have been collected from the MOBIDIC study. For each patient, 4 biopsies were collected, 2 or 3 for further investigations and 1 or 2 as back-up sample stored at Cell&Co (Clermont-Ferrand, France). The ileal specimens were introduced immediately into preweighed vials containing 1.8 mL of refrigerated DMEM with 15% glycerol. The vials were weighed to establish the weight of sample. Ideally, the size of the biopsies must be between 5 and 10 mg. After being frozen at −80° C., vials were sent to Cell&Co and stored at −80° C. upon receipt.

4. Aggregation of EB8018 to the Bacteria Isolated from Said Biopsies Collection

The aggregation to EB8018 of bacterial strains isolated from MOBIDIC biopsies has been outsourced to SMALTIS (Besangon, France). The main procedure is described below.

On day 1, biopsies were processed to retrieve adherent bacteria (extract A) and invasive bacteria (extract I). The detachment of the adherent bacteria from epithelial cells was done by sonication (30 kHZ, 300 w) and then the biopsy was washed by PBS, placed in LB broth for culture and tissues were breakdown for isolation of the invasive bacteria by vortexing. For both invasive and adherent extracts, 100 μL of extracts were plated on MH agar plates in order to observe the different bacteria morphotypes, 100 μL of extracts were inoculated in 3 mL of EC LB broth for further aggregation tests and the remaining was stored at −80° C. for long term conservation.

Extracts A and I were cultivated in LB broth for 2×24 hours and on day 3, the LB overnight cultures were used for aggregation assays with EB8018 compound. Three concentrations of EB8018 were tested (10 nM/100 nM/1 μM final concentrations), 500× working solutions were prepared in DMSO by 10-fold serial dilution from the 100 mM stock solutions, such as the final DMSO concentration in 96-well plates is 0.1%. DMSO (without any compound) was also diluted 500-fold in the LB in order to prepare LB with 0.2% DMSO (0.1% final concentration in the wells). 50 μL of solutions (EB8018 or DMSO) and then 50 μL of bacteria diluted suspensions were dispensed into the 96-well plate according the plate template. Plates were incubated for 5 hours at 37° C. under agitation in the SPARK 10M (96 rpm). Every hour, bacterial growth was measured and a picture of each well was taken using a SPARK10M. After 5 hours, the microplate was shacked and 10 min after, a picture was taken for aggregation assessment (aggregation was evaluated by a technician with comparison with DMSO). In case of aggregation for any extract and any concentration, morphotypes were isolated from the 2 O/N cultures by plating a $10^{-5/6}$ dilutions of the LB cultures used for the aggregations. Then, aggregation assays were performed on each morphotype with similar conditions as aggregation on extracts. Morphotypes that show aggregation in presence of EB8018 compound were identified (MALDI-TOF) and frozen at −80° C. On each plate, a positive control (LF82) and a negative control (LF82-ΔFimH) were used.

For extracts and isolated morphotypes, aggregation was primary evaluated by a technician and reported on SMAL-TIS technical reports as follows:
"−" no aggregation
"+/−−" very low aggregation
"+/−" moderate aggregation
"+" aggregation
"++" strong aggregation
"+++/++++" very strong aggregation When no aggregation was observed on extracts or in case of inconclusive evaluation (for example with observation of aggregation with the DMSO without any compound), a second biopsy was analysed following the same protocol.

After the analysis of all biopsies, in order to avoid any misinterpretation of aggregation and to standardize the results, Enterome had requested SMALTIS to do a final blind review of all results. For isolated morphotypes, Enterome had prepared PDFs with pictures taken at 4 h, 5 h and 5 h after shaking and strains IDs were anonymized. All pictures were reviewed by two independent technicians at SMALTIS and results were unblinded by Enterome. Aggregation of isolated morphotypes was evaluated by four levels: 'no aggregation', 'low/medium aggregation', 'aggregation' or 'inconclusive'.

5. Validation of the qPCR Analysis on Stool Samples 5.1. Stool samples from the MOBIDIC study were sent to Eurofins/GATC Biotech (Konstanz, Germany) for aliquoting and DNA isolation using the QIAamp Stool DNA mini kit. For each stool samples, three aliquots were obtained and we extracted the two first aliquots. For some stool samples, the third aliquot was also extracted. A quality control was performed by looking at the concentration and the degradation. The samples had been processed in two batches, a first batch of 30 samples and the remaining samples in a second batch. We observed smeared bands on gel electrophoresis for the first batch and some samples did not pass the quality controls. However, these quality checks have been adjusted by Eurofins/GATC as control for further sequencing, and we decided to use them for qPCR analysis by selecting the best aliquots.

121 DNA samples were sent to TATAA biocenter for qPCR analysis. The experiment was performed according to ISO 17025 accredited method "ME 5.4247 qPCR Analysis with MGS assays SYBR". All samples were analyzed on all 9 assays in duplicates. Overall the qPCR went well with no amplifying NTCs (template controls) except for one replicate in the p1p3 assay which showed late amplification (>Cq35). This was only a one well contamination and was thus not thought to affect the samples or prove any general contamination of the mastermix. The standard deviation between replicates was for the most part below 0,5 which is the criteria used in the method for acceptable spread between replicates. Some reactions reaching close to Cq 30 and above demonstrated an increase in SD between replicates, since this is close to or equal to the LOQ of the various assays. Raw data were sent by TATAA in Excel files and Cq values were normalized by Enterome. Only the accredited results were used normalization, the amplification values for all other samples were set to 0. Cq values were normalized by interpolation with the amplification curve after correction by inter-plate calibrator. Absolute concentrations of each assay for each sample were expressed as copies/μL.

5.2. Aggregation to EB8018 had been performed by Smaltis as described on the material and methods section. At the end, the aggregation was evaluated by looking at pictures for isolated morphotypes from one to two biopsies. The evaluation of aggregation was done in blind by two independent technicians at Smaltis and data were merged by the Data Management at Enterome. Through the 122 CD patients, 113 patients have had at least one biopsy evaluated by Smaltis. Among them, the results for 7 patients were inconclusive. For the remaining 106 patients, 69 patients (65%) had at least one morphotype that aggregated, 21 patients (20%) had sterile biopsies and 16 patients (15%) had no aggregation.

5.3. Association tests were performed between aggregation to EB8108 on biopsies and expression of FimS-On, FimS-Off and FimH targeting assays on stool samples. Association was evaluated by taking account for continuous expression of qPCR assays by performing Wilcoxon rank tests or by taking account for discrete variables (amplification vs. no amplification) by performing Pearson's chi-squared tests. Due to strong correlation between the assays, no correction for multiple testing was done. Hereafter we are reporting results considering the aggregation to EB8018 as two classes: 'aggregation' vs. 'no aggregation or no growth'. Addition results can be found on the statistical report for the MOBIDIC study.

5.4. Results 5.4.1. Results of the FimS OFF Assay

The following table presents the descriptive statistics of the FimS OFF-targeting assays and the p-values for the two tests (Wilcoxon and Pearson's chi-squared tests) and its significativity (S for significant or NS for non-significant).

TABLE 6

Descriptive statistics on the global population for FimS-OFF assays.

| Assay | Number of patients with aggregation | Number of patients with Abs of aggregation or No growth | Wilcoxon test | Pearson's chi-squared test |
|---|---|---|---|---|
| p1.p2 OFF (log10) | 68 | 37 | <0.001 (S) | 0.002 (S) |
| p3.p4 OFF (log10) | 68 | 37 | 0.032 (S) | 1.000 (NS)* |
| p5.p6 OFF (log10) | 68 | 37 | <0.001 (S) | 0.342 (NS)* |
| p7.p8 OFF (log10) | 68 | 37 | <0.001 (S) | 0.283 (NS)* |

*Fisher exact test was used instead of Pearson's chi-squared.

Figure 5:
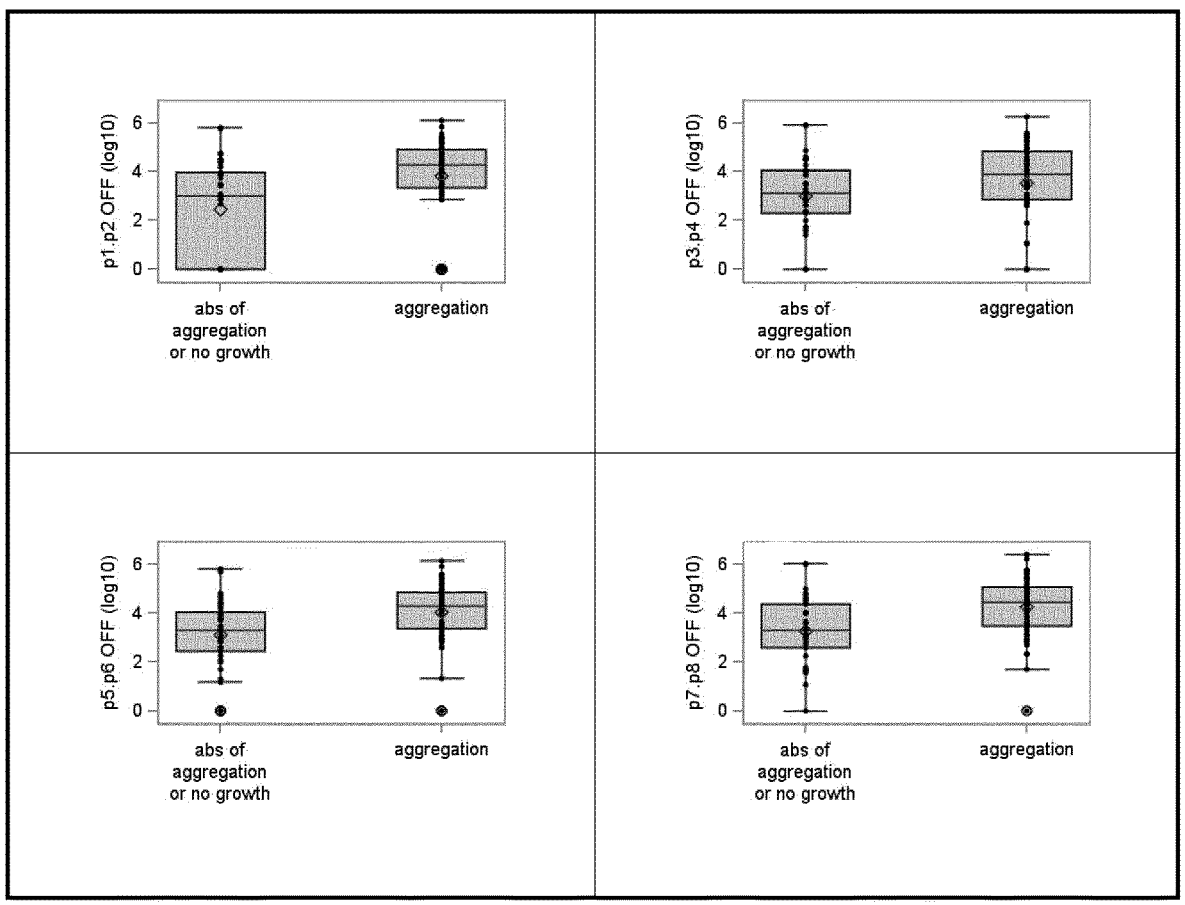
FIG. 5 discloses the distribution of FimS OFF-targeting assays in logarithmic scale, by group, on the global population of the MOBIDIC study.

The graphics in FIG. 5 present the distribution of FimS OFF-targeting assays in logarithmic scale, by group, on the global population.

5.4.2. Results of the FimS ON Assay

The following table presents the descriptive statistics of the FimS ON-targeting assays and the p-values for the two tests (Wilcoxon and Pearson's chi-squared tests) and its significativity (S for significant or NS for non significant).

TABLE 7

Descriptive statistics on the global population for FimS-ON assays

| Assay | Number of patients with aggregation | Number of patients with Abs of aggregation or No growth | Wilcoxon test | Pearson's chi-squared test |
|---|---|---|---|---|
| p1.p3 ON (log10) | 68 | 37 | 0.002 (S) | 0.009 (S) |
| p2.p4 ON (log10) | 68 | 37 | 0.007 (S) | 0.004 (S) |
| p5.p7 ON (log10) | 68 | 37 | <0.001 (S) | 0.010 (S) |
| p6.p8 ON (log10) | 68 | 37 | 0.001 (S) | <0.001 (S) |

Figure 6:
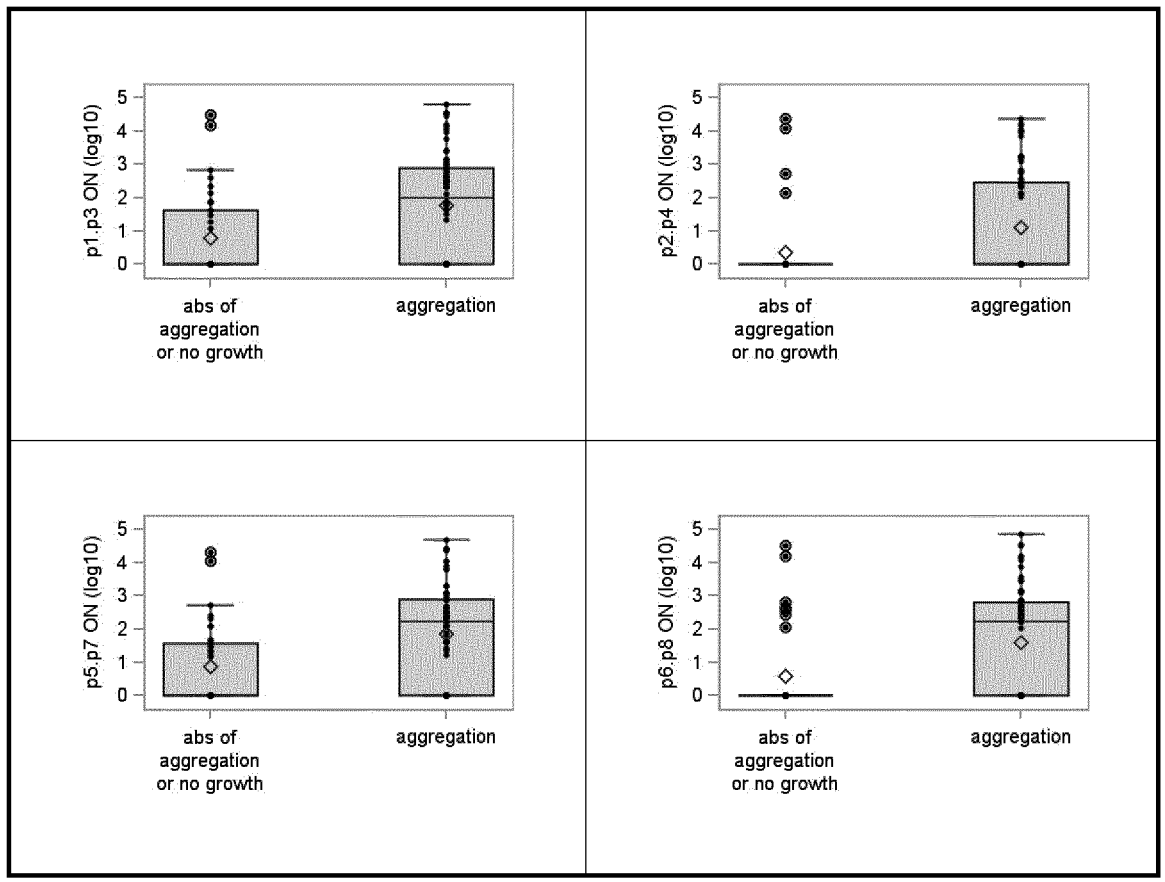
FIG. 6 discloses the distribution of FimS ON-targeting assays in logarithmic scale, by group, on the global population.

The graphics in FIG. 6 present the distribution of FimS ON-targeting assays in logarithmic scale, by group, on the global population.

5.4.3. These results showed a strong correlation between all qPCR markers and the aggregation to EB8018. However, the strongest association was obtained for FimS ON-targeting assays, in terms of amplitude (Wilcoxon rank tests) and detection/no detection of the sequence (Pearson's chi-squared tests). By looking specifically at the FimS-ON targeting assay p5p7, the following contingency table was obtained, using a threshold of 10 copies/µL, which corresponded to the limit of detection. The AUC value for this assay was 0.7.

TABLE 8

Contingency table for the classification of 'aggregation' vs. 'abs. of aggregation or no growth' with the On-targeting assays for FimS p5.p7 and a threshold of 10 copies/µL. This threshold corresponds to the limit of quantification.

| | Aggregation | Abs. of aggregation or No growth | |
|---|---|---|---|
| p5p ≥ 10 copies/µL | 47 | 16 | 74.60 |
| p5p7 < 10 copies/µL | 21 | 21 | 50.00 |
| | 69.11 | 56.75 | |

Figure 8:
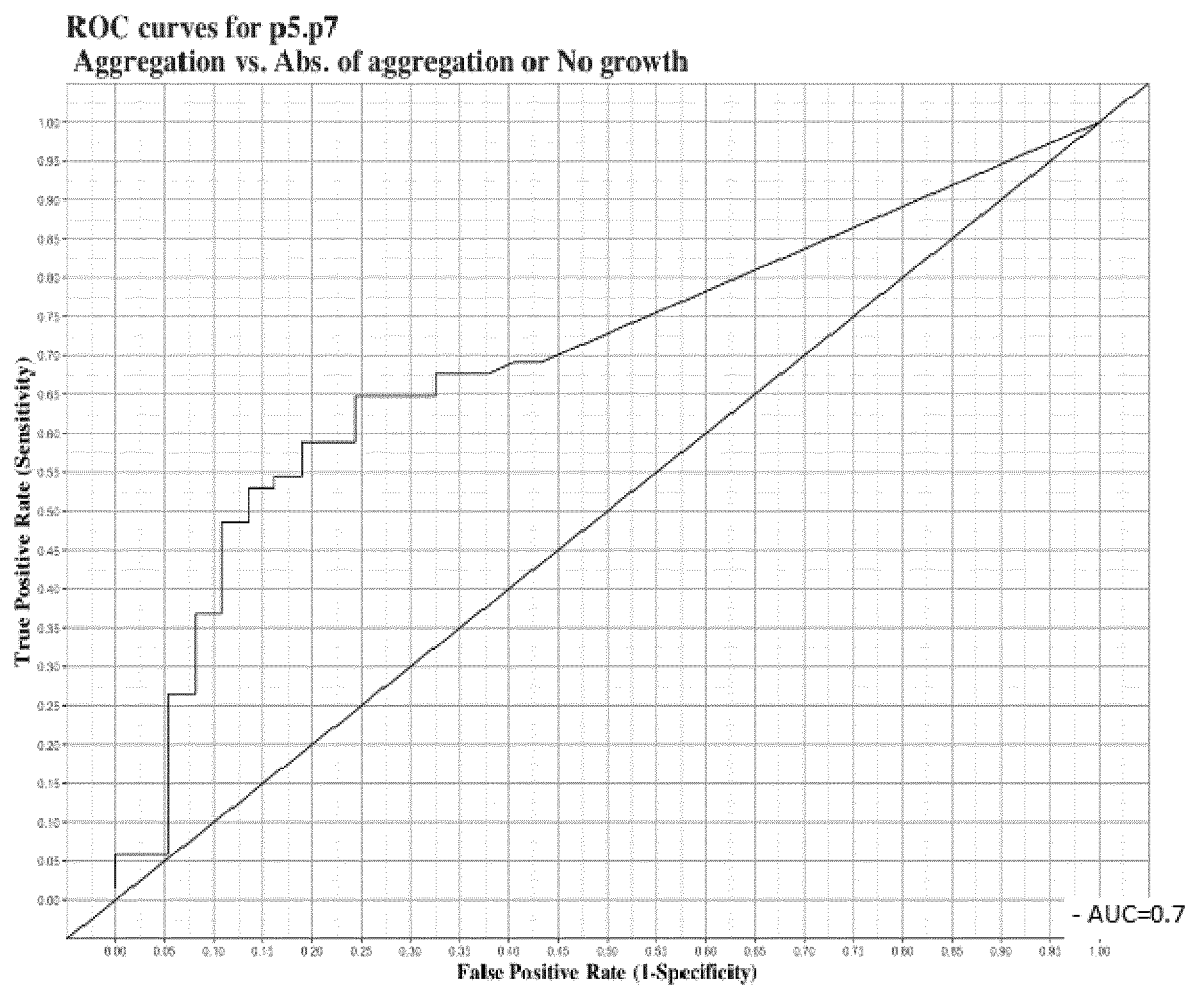
FIG. 8 shows the ROC curve for the assay p5p7. Sensitivity refers to aggregation and specificity to Abs. of aggregation or No growth.

FIG. 8 discloses the ROC curve obtained for this particular assay.

6. The FimH Assay

A qPCR assay targeting the *E. coli* gene FimH was also developed. The technical development and the technical validation were performed in compliance with ISO17025.

6.1. Selection of Candidate Regions for qPCR Primers and Design of Primers

Four regions on the FimH gene were selected for primer design. For each of the four regions, three assays were designed. Hydrolysis probe based assay design was carried out using Allele ID & Beacon designer (PREMIER Biosoft). The probes are labelled with FAM in the 5'-end and with IBFQ quencher in the 3'-end plus an internal ZEN quencher (PrimeTime ZEN probes, IDT). The probe sequences, sense and anti-sense primers for all assays are reported on the table below (Table 9).

TABLE 9 the probe sequences, sense and anti-sense primers for all assays.

| Assay name | Sequence Definition | Sequence Length | Probe Sequence | Sense Primer | Anti-sense Primer |
|---|---|---|---|---|---|
| FIMH_2_1 | 2149699\|FIMH | 912 | ACCTCTCCGGCAC AACCGCAGATGC (SEQ ID NO: 41) | CCTCTTACCGTT TATTGTGCGAAA (SEQ ID NO: 35) | ACGACGCGGT ATTGGTGAA (SEQ ID NO: 36) |
| FIMH_2_2 | 2149699\|FIMH | 912 | ACCTCTCCGGCAC AACCGCAGATGC (SEQ ID NO: 42) | TGTGCGAAAAGC CAAAACCTG (SEQ ID NO: 37) | ACGACGCGGT ATTGGTGAA (SEQ ID NO: 38) |
| FIMH_2_3 | 2149699\|FIMH | 912 | CGCCACCGGCCA CGGCTTATCC (SEQ ID NO: 43) | GCCGCGGGTTGT TTATAATTCG (SEQ ID NO: 39) | ACTGCTCACA GGCGTCAA (SEQ ID NO: 40) |

6.2. Development of the qPCR Assay

The technical development and validation of qPCR assays for FimH was conducted by TATAA biocenter.

After checking for correct amplification and linearity, the efficiency of PCR reactions was estimated for each assay and FIMH_2_1 was selected by maximization of the efficiency for further normalization. Finally, efficiency, LOD and LOQ values as well as normalization parameter were saved for further normalization of new samples (see table below for details).

TABLE 10

Normalization settings for the FimH assays.

| Patients/PCR product | Assays | slope | intercept | efficiency | LOQ (Copies/rxn) | LOD (Copies/rxn) | IPC Efficiency plates |
|---|---|---|---|---|---|---|---|
| AFA38_06 | FIMH_2_1 | −3.35 | 35.26 | 0.99 | 20 | 14.15 | 14.62 |

The following table presents the descriptive statistics of the FimH targeting assay and the p-value associated to the Wilcoxon test and its significativity.

TABLE 11

Descriptive statistics on the global population for the FimH assay

| Assay | Aggregation | Abs of aggregation or No growth | Wilcoxon test |
|---|---|---|---|
| FimH_2_1 (log10) | 68 (1) | 37 (0) | <0.001 (S) |

Figure 7:
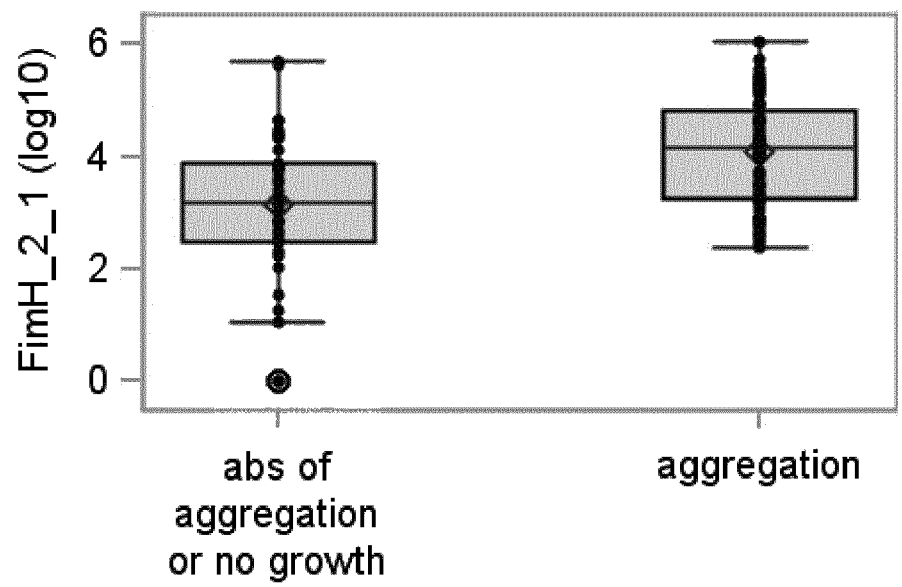
FIG. 7 discloses the distribution of FimH targeting assay in absence or in presence of aggregation.

The graphics in FIG. 7 present the distribution of FimH-targeting assays in logarithmic scale, by group, on the global population.

7. Association Between the Crohn Disease Activity Index (CDAI) and FimS ON

On the MOBIDIC Study, 35 patients were classified as 'active' (i.e., having a CDAI>150) and 75 patients were classified as 'non-active' (i.e., having a CDAI 150). Two FimS-ON assays were significantly associated with the disease activity (p1.p3 ON, p=0.027; p6.p8 ON, p=0.031). The CDAI score is well known in the art. It is described for example in Best et al, 1976.

Figure 9:
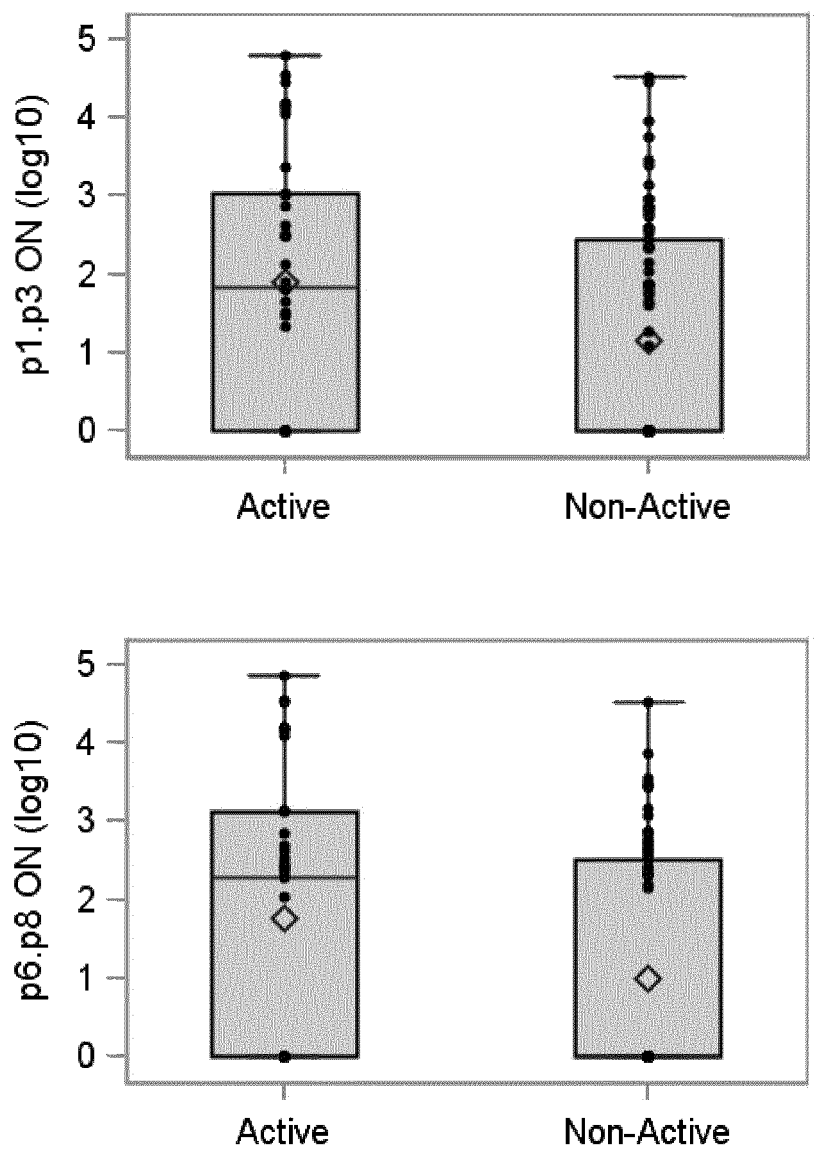
FIG. 9 discloses the distribution of FimS ON-targeting assays in logarithmic scale, by group of active or non-active patients, with the p1.p3 ON or the p6.p8 ON assays.

The graphics in FIG. 9 discloses the distribution of FimS ON-targeting assays in logarithmic scale, by group.

The MOBIDIC cohort (n=87) was analyzed by performing a Principal Component Analysis on clinical variables including endoscopic scores, protein levels (CRP, calprotectin), E. coli abundance and age and weight.

CRP and Calprotectin were correlated with endoscopic activity, as was previously reported (Sipponen, IBD, 2010 and Sipponen, IBD, 2008).

Figure 10:
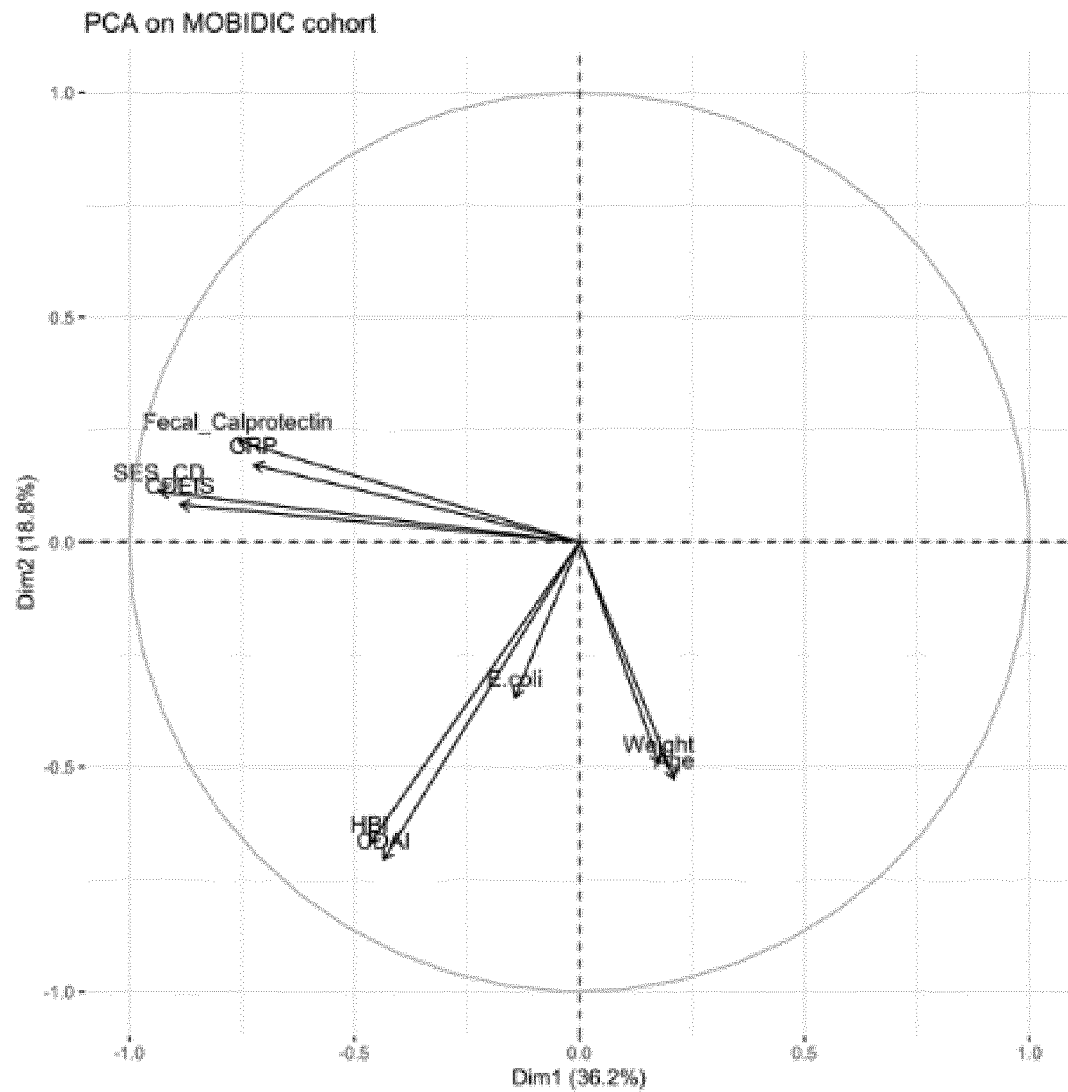
FIG. 10 discloses the Principal Component Analysis performed on the MOBIDIC cohort with several clinical variables.

E. coli was correlated with disease activity. Disease activity and E. coli were orthogonal to endoscopic activity. For example, the correlation between SES-CD and CDAI was 0.25 (spearman's coefficient) for MOBIDIC (see FIG. 10).

This is surprising, since the correlation between fecal markers and the disease activity or between the disease activity and the endoscopic activity has been shown to be weak (see Sipponen T, IBD, 2010 and Sipponen T, IBD, 2008).

In short, this means that:
i) the presence of FimH expressing bacteria in stool samples of the patients correlates with the activity of the disease, but not with the inflammatory level and symptoms;
ii) it is possible to prognose the Crohn's disease activity by assaying the presence of the biomarkers of the invention in whole stool samples, but not with ulceration markers such as SES-CD scores.

CONCLUSIONS

The sequencing of isolated strains allowed us to identify a strong association between the DNA sequences of the FimS region and aggregation to EB8018 ($p<0.0001$, Wilcoxon rank test). A technical development and validation of nine qPCR assays was done to target the FimS switch and the FimH gene. The MOBIDIC study allowed us to obtain stool and biopsies samples from CD patients. Bacterial DNA was isolated from stool samples and the nine qPCR assays were performed on the DNA samples. In the same time, aggregation tests to EB8018 were performed on isolated morphotype isolated from ileal biopsies. Statistical analyses shown a strong association between all qPCR assays and aggregation to EB8018, and especially for the FimS-ON targeting assays ($p<0.001$ for p5p7, Wilcoxon rank test).

BIBLIOGRAPHIC REFERENCES

Ayoib A. et al. *Appl Microbiol Biotechnol.* 2017
Barnich N et al., *Mol. Microbiol.* 2003, 48:781-794
Barnich N et al, *J. Clin. Invest* 2007, 117, 1566-1574
Barnich N et al, *Virulence* 2010 July-August; 1(4): 281-2
Barnich N. et al, *AGA Abstract* 2017
Bennett et al, *Am J of Pathology* 2016 May; 186(5):1166-79
Best W R et al, *Gastroenterology* 1976, March; 70(3):439-444
Baumgart M. et al., *ISME J.* 2007 September; 1(5):403-18
Bouckaert J et al. *Mol. Microbiol.* 2005, 55: 441-455.
Bouckaert J et al. *Mol. Microbiol.* 2006, 61: 1556-1568.
Bouckaert J et al. 2013 *Chemistry, a European Journal* 19: 7847-7855.
Boudeau J et al *Infect. Immun.* 1999, 67, 4499-4509
Boudeau J. et al, *Mol. Microbiol.* 2001; 39:1272-1284
Bringer M A. Et al, *Cellular Microbiology* (2006); 8(3), 471-484
Brument et al *Journal of Medicinal Chemistry* 2013, 56(13), 5395-5406
Burns L. et al., *Journal of Bacteriology*, May 2000, p. 2953-2959
Chalopin T. et al, *Org. Biomol. Chem.*, 2015
Chalopin T. et al, *J. Name* 00, 1-3, 2013
Chassaing et al., *J Clin Invest.* 2011 March; 121(3):966-75.
Cho et al. *Gastroenterology* 2011, 140(6), 1704-12. doi: 10.1053/j.gastro.2011.02.046
Cusumano C K et al, *Sci. Transl. Med.* 2011; 3:109ra15
Darfeuille-Michaud et al *Gastroenterology* 2004, 127 (2), 412-421
Dogan B. et al., *Inflamm Bowel Dis.* 2014; 0:1-14
Dreux N. et al *PLOS Pathogens* 2013, 9, 1, e1003141
Glasser A L. et al, *Infection and Immunity*, September 2001, p.5529-5537
Godon J J. et al, *Appl. Environ. Microbiol.* 1997
Holden N. et al., *Microbiology* 2007, 153:4138-4149
Klemm P., 1986, *The EMBO journal*, vol. 5, n° 6, pp. 1389-1393
Kulasekara H D et al., 1999, *Mol. Microbiol.* 31:1171-1181
Molodecky N A, et al. *Gastroenterology.* 2012
Moor et al., *Nature.* 2017 Apr. 27; 544(7651):498-502.
Mossman et al. *J Immunol.* 2008 Nov. 15; 181(10):6702-6

Mydock-McGrane L. et al., *Expert Opinion on Therapeutic Patents,* 26:2, 175-197, 2016
O'Brien et al., 2016, *Gut* 2016; 0:1-8
Simpson et al., *Infect Immun.* 2006 August; 74(8):4778-92
Sivignon A. et al., *MBio* 2015, nov 17; 6(6)
Sokurenko EV., *JOURNAL OF BACTERIOLOGY,* July 1995, p. 3680-3686
Spaulding et al., *Nature* 2017, Jun. 22; 546(7659):528-532.
Sipponen T., *Inflamm. Bowel. Dis.* Vol. 14, Number I, January 2008
Sipponen T., *Inflamm. Bowel. Dis.* Vol. 16, Number 12, December 2010
Totsika M. et al, *JID,* 2013: 208
van der Woude and Baumler. *Clin Microbiol Rev.* 2004 July; 17(3): 581-611.
Wellens et al. *PLoS ONE* 2008, 3(4), e2040
Yakovenko O., *PNAS* 2015, vol. 112, No. 32, pp. 9884-9889
Zhang H et al., *PNAS* 2016, vol. 113, No. 15, pp. 4182-4187

The invention claimed is:

1. A method for treating a human subject suffering from Crohn Disease (CD), said method comprising the steps of:
   a) isolating a nucleotide fraction of a stool sample from said subject,
   b) detecting expression of the fimH gene in said nucleotide fraction by measuring the switch of the *Escherichia coli* fim operon transcription from OFF to ON in a nucleotide fraction of said stool sample to calculate an ON/(ON+OFF) ratio of the fimH gene, and comparing the ON/(ON+OFF) ratio with a reference value of 15%,
   c) administering a mannose derivative FimH blocker to subjects whose nucleotide fraction has an ON/(ON+OFF) ratio higher than said reference value of 15%.

2. The method of claim 1, wherein said detecting step comprises measuring the presence of the ON region of SEQ ID NO:14 of the fim operon transcription in said stool sample.

3. The method of claim 1, wherein said detecting step comprises measuring the presence of the ON region of SEQ ID NO:14 of the fim operon transcription in said stool sample by using the primer pair of SEQ ID NO:5&7.

4. The method of claim 1, wherein said detecting step comprises measuring the presence of the OFF region of SEQ ID NO:13 of the fim operon transcription in said stool sample.

5. The method of claim 1, wherein said detecting step comprises measuring the presence of the OFF region of SEQ ID NO:13 of the fim operon transcription in said stool sample, by using the primer pair of SEQ ID NO:5&8.

6. The method of claim 1, wherein said mannose derivative FimH blocker has the formula:

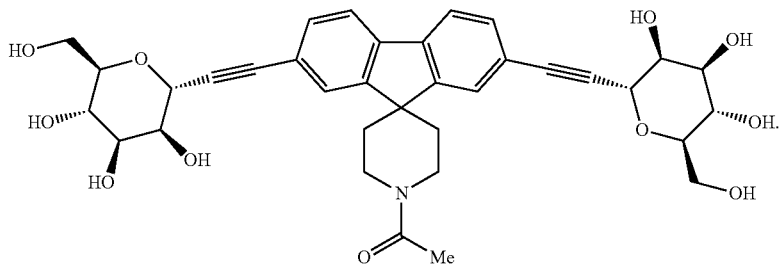

7. The method of claim 1, wherein the mannose derivative FimH blocker is selected from Heptylmannose, Thiazolyl-mannosides, and ZFH-04269.

8. The method of claim 1, wherein the ON/(ON+OFF) ratio for the stool sample is more than 30%.

* * * * *

SEQUENCE LISTING

```
<160> NUMBER OF SEQ ID NOS: 43

<210> SEQ ID NO 1
<211> LENGTH: 20
<212> TYPE: DNA
<213> ORGANISM: artificial
<220> FEATURE:
<223> OTHER INFORMATION: primer p1

<400> SEQUENCE: 1
gtaatgctgc tcgttttgcc                                              20

<210> SEQ ID NO 2
<211> LENGTH: 22
<212> TYPE: DNA
<213> ORGANISM: artificial
<220> FEATURE:
<223> OTHER INFORMATION: primer p2

<400> SEQUENCE: 2
catatagcgg aggtgatgtg aa                                           22

<210> SEQ ID NO 3
<211> LENGTH: 20
<212> TYPE: DNA
<213> ORGANISM: artificial
<220> FEATURE:
<223> OTHER INFORMATION: primer p3

<400> SEQUENCE: 3
tgcgcgatgc tttcctctat                                              20

<210> SEQ ID NO 4
<211> LENGTH: 15
<212> TYPE: DNA
<213> ORGANISM: artificial
<220> FEATURE:
<223> OTHER INFORMATION: primer p4

<400> SEQUENCE: 4
gcgcaagcgg cgtta                                                   15

<210> SEQ ID NO 5
<211> LENGTH: 19
<212> TYPE: DNA
<213> ORGANISM: artificial
<220> FEATURE:
<223> OTHER INFORMATION: primer p5

<400> SEQUENCE: 5
cggattatgg gaaagaaat                                               19

<210> SEQ ID NO 6
<211> LENGTH: 19
<212> TYPE: DNA
```

```
<213> ORGANISM: artificial
<220> FEATURE:
<223> OTHER INFORMATION: primer p6

<400> SEQUENCE: 6
tcaaacagtt agatgcttt                                              19

<210> SEQ ID NO 7
<211> LENGTH: 18
<212> TYPE: DNA
<213> ORGANISM: artificial
<220> FEATURE:
<223> OTHER INFORMATION: primer p7

<400> SEQUENCE: 7
cgatgctttc ctctatga                                               18

<210> SEQ ID NO 8
<211> LENGTH: 18
<212> TYPE: DNA
<213> ORGANISM: artificial
<220> FEATURE:
<223> OTHER INFORMATION: primer p8

<400> SEQUENCE: 8
ttgttttgtc aacgagtt                                               18

<210> SEQ ID NO 9
<211> LENGTH: 98
<212> TYPE: DNA
<213> ORGANISM: escherichia coli
<220> FEATURE:
<221> NAME/KEY: misc_feature
<223> OTHER INFORMATION: switch region of FimS

<400> SEQUENCE: 9
ttaactaatt gataataaag ttaaaaaaca aataaataca agacaattgg ggccaaactg    60
tctatatcat aaataagtta cgtatttttt ctcaagca                           98

<210> SEQ ID NO 10
<211> LENGTH: 87
<212> TYPE: DNA
<213> ORGANISM: escherichia coli
<220> FEATURE:
<221> NAME/KEY: misc_feature
<223> OTHER INFORMATION: Switch region of FimS

<400> SEQUENCE: 10
agtcaaactc gttgacaaaa caaagtgtac agaacgactg cccatgtcga tttagaaata    60 gttttttta aggaaagcag catgaaa                                        87

<210> SEQ ID NO 11
<211> LENGTH: 9
<212> TYPE: DNA
<213> ORGANISM: artificial
<220> FEATURE:
<223> OTHER INFORMATION: IRR1 within the fimS gene
<220> FEATURE:
<221> NAME/KEY: misc_feature
<223> OTHER INFORMATION: IRR 1 of the fim operon (within FimS)

<400> SEQUENCE: 11 ttggggcca                                                           9

<210> SEQ ID NO 12
```

```
<211> LENGTH: 9
<212> TYPE: DNA
<213> ORGANISM: artificial
<220> FEATURE:
<223> OTHER INFORMATION: IRR2 within the FimS region

<400> SEQUENCE: 12 tggccccaa                                                                     9

<210> SEQ ID NO 13
<211> LENGTH: 1633
<212> TYPE: DNA
<213> ORGANISM: escherichia coli
<220> FEATURE:
<221> NAME/KEY: misc_feature
<223> OTHER INFORMATION: FimE-fimS-FimA region OFF position

<400> SEQUENCE: 13
gtgagtaaac gtcgttatct taccggtaaa gaagttcagg ccatgatgca ggcggtgtgt      60
tacggggcaa cgggagccag agattattgt cttattctgt tggcatatcg gcatgggatg     120
cgtattagtg aactgcttga tctgcattat caggatcttg accttaatga aggtcgaata     180
aatattcgcc gactgaagaa cggattttct accgttcacc cgttacgttt tgatgagcgt     240
gaagccgtgg aacgctggac ccaggaacgt gctaactgga aaggcgctga ccggaccgac     300
gctatattta tttctcgccg tgggagtcgg cttttctcgcc agcaggccta tcgcattatt     360
cgcgatgccg gtattgaagc tggaaccgta acgcagactc atcctcatat gttaaggcat     420
gcttgtggtt atgaactggc tgagcgtggt gcagatacccc gtttaattca ggattatctc     480
gggcatcgaa atattcgcca tactgtgcgt tataccgcca gtaatgctgc tcgttttgcc     540
ggattatggg aaagaaataa tctcataaac gaaaaattaa aaagagaaga gcttgatttt     600
aactaattga taataaagtt aaaaaacaaa taaatacaag acaattgggg ccaaactgtc     660
tatatcataa ataagttacg tatttttttct caagcataaa aatattaaaa aacgacaaaa     720
agcatctaac tgtttgatat ataaattatt tctcttgtaa attaatttca catcacctcc     780
gctatatgta aagctaacgt ttctgtagct cgacgcaact tcctcattct tctctccaaa     840
aaccacctca tgcaatataa aaaactgcaa ataaagataa ctatagaaca ttaagccaac     900
aaataaactg aaaaagtttg tgcgcgatgc tttcctctat gagtcaaaat ggccccaaat     960
gtttcatctt ttgggggaaa actgtgcagt gttggcagtc aaactcgttg acaaaacaaa    1020
gtgtacagaa cgactgccca tgtcgattta gaaatagttt ttttaaagga aagcagcatg    1080
aaaattaaaa ctctggcaat tgttgttctg tcggctctgt ccctgagttc tacagcggct    1140
ctggctgata ctacacccac gacggtaaat ggtgggaccg ttcactttaa aggggaagtt    1200
gttaacgccg cttgcgcagt tgatgcaggc tctgttgatc aaaccgttca gttaggacag    1260
gttcgtaccg ccactttgaa gcaggctgga gcaaccagct ctgctgtcgg ttttaacatt    1320
cagctgaatg attgcgatac cactgttgcc acaaaagccg ctgttgcctt cttggggacg    1380
gcgattgaca gtactcatcc taaagtcctg gctctacaga gttcagctgc gggtagcgca    1440
acaaacgttg gcgtgcagat tctggacaga acaggtaatg agctgacgct ggacggtgcg    1500
acatttagtg cagaaacaac cctgaataac ggtactaaca ccattccgtt ccaggcgcgt    1560
tattttgcaa ccggtgctgc aaccccaggt gctgctaatg cggatgcgac cttcaaggtt    1620
cagtatcaat aac                                                        1633

<210> SEQ ID NO 14
```

<211> LENGTH: 1573
<212> TYPE: DNA
<213> ORGANISM: escherichia coli
<220> FEATURE:
<221> NAME/KEY: misc_feature
<223> OTHER INFORMATION: fimE-fimS-fimA ON position

<400> SEQUENCE: 14

```
tacggggcaa cgggagccag agattattgt cttattctgt tggcatatcg gcatgggatg        60
cgtattagtg aactgcttga tctgcattat caggatcttg accttaatga aggtcgaata       120
aatattcgcc gactgaagaa cggattttct accgttcacc cgttacgttt tgatgagcgt       180
gaagccgtgg aacgctggac ccaggaacgt gctaactgga aagcgctgaa ccggaccgac       240
gctatattta tttctcgccg tgggagtcgg cttcctcgcc agcaggccta tcgcattatt       300
cgcgatgccg gtattgaagc tggaaccgta acgcagactc atcctcatat gttaaggcat       360
gcttgtggtt atgaactggc tgagcgtggt gcagataccc gtttaattca ggattatctc       420
gggcatcgaa atattcgcca tactgtgcgt tataccgcca gtaatgctgc tcgttttgcc       480
ggattatggg aaagaaataa tctcataaac gaaaaattaa aagagaaga agcttgattt       540
aactaattga taataaagtt aaaaaacaaa taaatacaag acaattgggg ccattttgac       600
tcatagagga aagcatcgcg cacaaacttt ttcagtttat ttgttggctt aatgttctat       660
agttatcttt atttgcagtt ttttatattg catgaggtgg ttttttggaga gaagaatgag       720
gaagttgcgt cgagctacag aaacgttagc tttacatata gcggaggtga tgtgaaatta       780
atttacaaga gaataatttt atatatcaaa cagttagatg cttttttgtcg tttttttaata      840
tttttatgct tgagaaaaaa tacgtaactt atttatgata tagacagttt ggccccaaat       900
gtttcatctt ttgggggaaa actgtgcagt gttggcagtc aaactcgttg acaaaacaaa       960
gtgtacagaa cgactgccca tgtcgatta gaaatagttt tttaaagga aagcagcatg       1020
aaaattaaaa ctctggcaat tgttgttctg tcggctctgt ccctgagttc tacagcggct      1080
ctggctgata ctacacccac gacggtaaat ggtgggaccg ttcactttaa aggggaagtt      1140
gttaacgccg cttgcgcagt tgatgcaggc tctgttgatc aaaccgttca gttaggacag      1200
gttcgtaccg ccactttgaa gcaggctgga gcaaccagct ctgctgtcgg ttttaacatt      1260
cagctgaatg attgcgatac cactgttgcc acaaaagccg ctgttgcctt cttggggacg      1320
gcgattgaca gtactcatcc taaagtcctg gctctacaga gttcagctgc gggtagcgca      1380
acaaacgttg gcgtgcagat tctggacaga acaggtaatg agctgacgct ggacggtgcg      1440
acatttagtg cagaaacaac cctgaataac ggtactaaca ccattccgtt ccaggcgcgt      1500
tattttgcaa ccggtgctgc aacccccaggt gctgctaatg cggatgcgac cttcaaggtt      1560
cagtatcaat aac                                                         1573
```

<210> SEQ ID NO 15
<211> LENGTH: 598
<212> TYPE: DNA
<213> ORGANISM: escherichia coli
<220> FEATURE:
<221> NAME/KEY: misc_feature
<223> OTHER INFORMATION: fimE in the OFF position

<400> SEQUENCE: 15

```
gtgagtaaac gtcgttatct taccggtaaa gaagttcagg ccatgatgca ggcggtgtgt        60
tacggggcaa cgggagccag agattattgt cttattctgt tggcatatcg gcatgggatg       120
cgtattagtg aactgcttga tctgcattat caggatcttg accttaatga aggtcgaata       180
```

```
aatattcgcc gactgaagaa cggatttcct accgttcacc cgttacgttt tgatgagcgt    240
gaagccgtgg aacgctggac ccaggaacgt gctaactgga aaggcgctga ccggaccgac    300
gctatattta tttctcgccg tgggagtcgg ctttctcgcc agcaggccta tcgcattatt    360
cgcgatgccg gtattgaagc tggaaccgta acgcagactc atcctcatat gttaaggcat    420
gcttgtggtt atgaactggc tgagcgtggt gcagataccc gtttaattca ggattatctc    480
gggcatcgaa atattcgcca tactgtgcgt tataccgcca gtaatgctgc tcgttttgcc    540
ggattatggg aaagaaataa tctcataaac gaaaaattaa aagagaaga agcttgat      598
```

<210> SEQ ID NO 16
<211> LENGTH: 485
<212> TYPE: DNA
<213> ORGANISM: escherichia coli
<220> FEATURE:
<221> NAME/KEY: misc_feature
<223> OTHER INFORMATION: fimS in the OFF position

<400> SEQUENCE: 16

```
ttaactaatt gataataaag ttaaaaaaca aataaataca agacaattgg ggccaaactg     60
tctatatcat aaataagtta cgtatttttt ctcaagcata aaaatattaa aaaacgacaa    120
aaagcatcta actgtttgat atataaatta tttctcttgt aaattaattt cacatcacct    180
ccgctatatg taaagctaac gtttctgtag ctcgacgcaa cttcctcatt cttctctcca    240 aaaccacct catgcaatat aaaaaactgc aaataaagat aactatagaa cattaagcca     300
acaaataaac tgaaaagtt tgtgcgcgat gctttcctct atgagtcaaa atggccccaa    360
atgtttcatc ttttgggga aaactgtgca gtgttggcag tcaaactcgt tgacaaaaca    420
aagtgtacag aacgactgcc catgtcgatt tagaaatagt ttttttaaag gaaagcagca    480
tgaaa                                                              485
```

<210> SEQ ID NO 17
<211> LENGTH: 550
<212> TYPE: DNA
<213> ORGANISM: escherichia coli
<220> FEATURE:
<221> NAME/KEY: misc_feature
<223> OTHER INFORMATION: fimA in the OFF position

<400> SEQUENCE: 17

```
attaaaactc tggcaattgt tgttctgtcg gctctgtccc tgagttctac agcggctctg     60
gctgatacta cacccacgac ggtaaatggt gggaccgttc actttaaagg ggaagttgtt    120
aacgccgctt gcgcagttga tgcaggctct gttgatcaaa ccgttcagtt aggacaggtt    180
cgtaccgcca ctttgaagca ggctggagca accagctctg ctgtcggttt taacattcag    240
ctgaatgatt gcgataccac tgttgccaca aaagccgctg ttgccttctt ggggacggcg    300
attgacagta ctcatcctaa agtcctggct ctacagagtt cagctgcggg tagcgcaaca    360
aacgttggcg tgcagattct ggacagaaca ggtaatgagc tgacgctgga cggtgcgaca    420
tttagtgcag aaacaacccct gaataacggt actaacacca ttccgttcca ggcgcgttat    480
tttgcaaccg gtgctgcaac cccaggtgct gctaatgcgg atgcgacctt caaggttcag    540
tatcaataac                                                         550
```

<210> SEQ ID NO 18
<211> LENGTH: 598
<212> TYPE: DNA

<213> ORGANISM: escherichia coli
<220> FEATURE:
<221> NAME/KEY: misc_feature
<223> OTHER INFORMATION: fimE in the ON position

<400> SEQUENCE: 18

| | | | | | |
|---|---|---|---|---|---|
| gtgagtaaac | gtcgttatct | taccggtaaa | gaagttcagg | ccatgatgca | ggcggtgtgt | 60 |
| tacgggcaa | cgggagccag | agattattgt | cttattctgt | tggcatatcg | gcatgggatg | 120 |
| cgtattagtg | aactgcttga | tctgcattat | caggatcttg | accttaatga | aggtcgaata | 180 |
| aatattcgcc | gactgaagaa | cggatttttct | accgttcacc | cgttacgttt | tgatgagcgt | 240 |
| gaagccgtgg | aacgctggac | ccaggaacgt | gctaactgga | aaggcgctga | ccggaccgac | 300 |
| gctatattta | tttctcgccg | tgggagtcgg | ctttctcgcc | agcaggccta | tcgcattatt | 360 |
| cgcgatgccg | gtattgaagc | tggaaccgta | acgcagactc | atcctcatat | gttaaggcat | 420 |
| gcttgtggtt | atgaactggc | tgagcgtggt | gcagataccc | gtttaattca | ggattatctc | 480 |
| gggcatcgaa | atattcgcca | tactgtgcgt | ataccgcca | gtaatgctgc | tcgttttgcc | 540 |
| ggattatggg | aaagaaataa | tctcataaac | gaaaaattaa | aagagaaga | agcttgat | 598 |

<210> SEQ ID NO 19
<211> LENGTH: 485
<212> TYPE: DNA
<213> ORGANISM: escherichia coli
<220> FEATURE:
<221> NAME/KEY: misc_feature
<223> OTHER INFORMATION: fimS in the ON position

<400> SEQUENCE: 19

| | | | | | |
|---|---|---|---|---|---|
| ttaactaatt | gataataaag | ttaaaaaaca | aataaataca | agacaattgg | ggccattttg | 60 |
| actcatagag | gaaagcatcg | cgcacaaact | ttttcagttt | atttgttggc | ttaatgttct | 120 |
| atagttatct | ttatttgcag | ttttttatat | tgcatgaggt | ggttttttgga | gagaagaatg | 180 |
| aggaagttgc | gtcgagctac | agaaacgtta | gctttacata | tagcggaggt | gatgtgaaat | 240 |
| taatttacaa | gagaaataat | ttatatatca | aacagttaga | tgcttttttgt | cgttttttaa | 300 |
| tatttttatg | cttgagaaaa | aatacgtaac | ttatttatga | tatagacagt | ttggccccaa | 360 |
| atgtttcatc | tttttggggga | aaactgtgca | gtgttggcag | tcaaactcgt | tgacaaaaca | 420 |
| aagtgtacag | aacgactgcc | catgtcgatt | tagaaatagt | ttttttaaag | gaaagcagca | 480 |
| tgaaa | | | | | | 485 |

<210> SEQ ID NO 20
<211> LENGTH: 550
<212> TYPE: DNA
<213> ORGANISM: escherichia coli
<220> FEATURE:
<221> NAME/KEY: misc_feature
<223> OTHER INFORMATION: fimA in the ON position

<400> SEQUENCE: 20

| | | | | | |
|---|---|---|---|---|---|
| attaaaactc | tggcaattgt | tgttctgtcg | gctctgtccc | tgagttctac | agcggctctg | 60 |
| gctgatacta | cacccacgac | ggtaaatggt | gggaccgttc | actttaaagg | ggaagttgtt | 120 |
| aacgccgctt | gcgcagttga | tgcaggctct | gttgatcaaa | ccgttcagtt | aggacaggtt | 180 |
| cgtaccgcca | ctttgaagca | ggctggagca | accagctctg | ctgtcggttt | taacattcag | 240 |
| ctgaatgatt | gcgataccac | tgttgccaca | aaagccgctg | ttgccttctt | ggggacggcg | 300 |
| attgacagta | ctcatcctaa | agtcctggct | ctacagagtt | cagctgcggg | tagcgcaaca | 360 |

-continued

| | |
|---|---|
| aacgttggcg tgcagattct ggacagaaca ggtaatgagc tgacgctgga cggtgcgaca | 420 |
| tttagtgcag aaacaaccct gaataacggt actaacacca ttccgttcca ggcgcgttat | 480 |
| tttgcaaccg gtgctgcaac cccaggtgct gctaatgcgg atgcgacctt caaggttcag | 540 |
| tatcaataac | 550 |

<210> SEQ ID NO 21
<211> LENGTH: 100
<212> TYPE: DNA
<213> ORGANISM: escherichia coli
<220> FEATURE:
<221> NAME/KEY: misc_feature
<223> OTHER INFORMATION: fimE 1_100

<400> SEQUENCE: 21

| | |
|---|---|
| gtgagtaaac gtcgttatct taccggtaaa gaagttcagg ccatgatgca ggcggtgtgt | 60 |
| tacggggcaa cgggagccag agattattgt cttattctgt | 100 |

<210> SEQ ID NO 22
<211> LENGTH: 100
<212> TYPE: DNA
<213> ORGANISM: escherichia coli
<220> FEATURE:
<221> NAME/KEY: misc_feature
<223> OTHER INFORMATION: fimE 101_200

<400> SEQUENCE: 22

| | |
|---|---|
| tggcatatcg gcatgggatg cgtattagtg aactgcttga tctgcattat caggatcttg | 60 |
| accttaatga aggtcgaata atattcgcc gactgaagaa | 100 |

<210> SEQ ID NO 23
<211> LENGTH: 100
<212> TYPE: DNA
<213> ORGANISM: escherichia coli
<220> FEATURE:
<221> NAME/KEY: misc_feature
<223> OTHER INFORMATION: fimE 201_300

<400> SEQUENCE: 23

| | |
|---|---|
| cggattttct accgttcacc cgttacgttt tgatgagcgt gaagccgtgg aacgctggac | 60 |
| ccaggaacgt gctaactgga aaggcgctga ccggaccgac | 100 |

<210> SEQ ID NO 24
<211> LENGTH: 100
<212> TYPE: DNA
<213> ORGANISM: escherichia coli
<220> FEATURE:
<221> NAME/KEY: misc_feature
<223> OTHER INFORMATION: fimE 301_400

<400> SEQUENCE: 24

| | |
|---|---|
| gctatattta tttctcgccg tgggagtcgg ctttctcgcc agcaggccta tcgcattatt | 60 |
| cgcgatgccg gtattgaagc tggaaccgta acgcagactc | 100 |

<210> SEQ ID NO 25
<211> LENGTH: 100
<212> TYPE: DNA
<213> ORGANISM: escherichia coli
<220> FEATURE:
<221> NAME/KEY: misc_feature
<223> OTHER INFORMATION: fimE 401_500

<400> SEQUENCE: 25
atcctcatat gttaaggcat gcttgtggtt atgaactggc tgagcgtggt gcagataccc     60
gtttaattca ggattatctc gggcatcgaa atattcgcca                            100

<210> SEQ ID NO 26
<211> LENGTH: 98
<212> TYPE: DNA
<213> ORGANISM: escherichia coli
<220> FEATURE:
<221> NAME/KEY: misc_feature
<223> OTHER INFORMATION: fimE 501_597

<400> SEQUENCE: 26
tactgtgcgt tataccgcca gtaatgctgc tcgttttgcc ggattatggg aaagaaataa     60
tctcataaac gaaaaattaa aaagagaaga agcttgat                              98

<210> SEQ ID NO 27
<211> LENGTH: 98
<212> TYPE: DNA
<213> ORGANISM: escherichia coli
<220> FEATURE:
<221> NAME/KEY: misc_feature
<223> OTHER INFORMATION: fimS 1_100

<400> SEQUENCE: 27
ttaactaatt gataataaag ttaaaaaaca aataaataca agacaattgg ggccaaactg     60
tctatatcat aaataagtta cgtattttt ctcaagca                               98

<210> SEQ ID NO 28
<211> LENGTH: 100
<212> TYPE: DNA
<213> ORGANISM: escherichia coli
<220> FEATURE:
<221> NAME/KEY: misc_feature
<223> OTHER INFORMATION: fimS 101_200

<400> SEQUENCE: 28 taaaatatt aaaaaacgac aaaaagcatc taactgtttg atatataaat tatttctctt      60
gtaaattaat ttcacatcac ctccgctata tgtaaagcta                            100

<210> SEQ ID NO 29
<211> LENGTH: 100
<212> TYPE: DNA
<213> ORGANISM: escherichia coli
<220> FEATURE:
<221> NAME/KEY: misc_feature
<223> OTHER INFORMATION: FimS 201_300

<400> SEQUENCE: 29
acgtttctgt agctcgacgc aacttcctca ttcttctctc caaaaccac ctcatgcaat      60 ataaaaaact gcaaataaag ataactatag aacattaagc                            100

<210> SEQ ID NO 30
<211> LENGTH: 100
<212> TYPE: DNA
<213> ORGANISM: escherichia coli
<220> FEATURE:
<221> NAME/KEY: misc_feature
<223> OTHER INFORMATION: fimS 301_400

<400> SEQUENCE: 30
caacaaataa actgaaaaag tttgtgcgcg atgctttcct ctatgagtca aaatggcccc     60
aaatgtttca tcttttgggg gaaaactgtg cagtgttggc                            100

<210> SEQ ID NO 31
<211> LENGTH: 87
<212> TYPE: DNA
<213> ORGANISM: escherichia coli
<220> FEATURE:
<221> NAME/KEY: misc_feature
<223> OTHER INFORMATION: fimS 401_488

<400> SEQUENCE: 31
agtcaaactc gttgacaaaa caaagtgtac agaacgactg cccatgtcga tttagaaata     60 gttttttttaa aggaaagcag catgaaa                                         87

<210> SEQ ID NO 32
<211> LENGTH: 100
<212> TYPE: DNA
<213> ORGANISM: escherichia coli
<220> FEATURE:
<221> NAME/KEY: misc_feature
<223> OTHER INFORMATION: fimA 101_200

<400> SEQUENCE: 32
actttaaagg ggaagttgtt aacgccgctt gcgcagttga tgcaggctct gttgatcaaa     60
ccgttcagtt aggacaggtt cgtaccgcca ctttgaagca                          100

<210> SEQ ID NO 33
<211> LENGTH: 100
<212> TYPE: DNA
<213> ORGANISM: escherichia coli
<220> FEATURE:
<221> NAME/KEY: misc_feature
<223> OTHER INFORMATION: fimA 401_500

<400> SEQUENCE: 33
tgacgctgga cggtgcgaca tttagtgcag aaacaaccct gaataacggt actaacacca     60
ttccgttcca ggcgcgttat tttgcaaccg gtgctgcaac                          100

<210> SEQ ID NO 34
<211> LENGTH: 912
<212> TYPE: DNA
<213> ORGANISM: Escherichia coli
<220> FEATURE:
<221> NAME/KEY: misc_feature
<223> OTHER INFORMATION: FimH gene

<400> SEQUENCE: 34
atgattgtaa tgaaacgagt tattaccctg tttgctgtac tgctgatggg ctggtcggta     60
aatgcctggt cattcgcctg taaaaccgcc aatggtaccg caatccctat tggcggtggc    120
agcgccaatg tttatgtaaa ccttgcgcct gccgtgaatg tggggcaaaa cctggtcgtg    180
gatctttcga cgcaaatctt tgccataac gattacccgg aaaccattac agattatgtc    240
acactgcaac gaggctcggc ttatggcggc gtgttatcta atttttccgg gaccgtaaaa    300
tataatggca gtagctatcc ttttcctact accagcgaaa cgccgcgggt tgtttataat    360
tcgagaacgg ataagccgtg gccggtggcg ctttattga cgcctgtgag cagtgcgggg    420
ggagtggcga ttaaagctgg ctcattaatt gccgtgctaa ttttgcgaca gaccaacaac    480
tataacagcg atgatttcca gtttgtgtgg aatatttacg ccaataatga tgtggtggtg    540
cctactggcg gctgtgatgt ttctgctcgt gatgtcaccg ttactctgcc ggactaccct    600
ggttcagtgc cgcttcctct taccgtttat tgtgcgaaaa gccaaaacct ggggtattac    660
ctctccggca caaccgcaga tgcgggcaac tcgatttca ccaataccgc gtcgttttca    720

```
ccagcgcagg gcgtcggcgt acagttgacg cgcaacggta cgattattcc agcgaataac    780
acggtatcgt taggagtagt agggacttcg gcggtaagtc tgggattaac ggcaaattac    840
gcacgtaccg gagggcaggt gactgcaggg aatgtgcaat cgattattgg cgtaactttt    900
gtttatcaat aa                                                         912
```

```
<210> SEQ ID NO 35
<211> LENGTH: 24
<212> TYPE: DNA
<213> ORGANISM: artificial
<220> FEATURE:
<223> OTHER INFORMATION: primer sens FimH_2_1

<400> SEQUENCE: 35
cctcttaccg tttattgtgc gaaa                                            24

<210> SEQ ID NO 36
<211> LENGTH: 19
<212> TYPE: DNA
<213> ORGANISM: artificial
<220> FEATURE:
<223> OTHER INFORMATION: primer antisens FimH_2_1

<400> SEQUENCE: 36
acgacgcggt attggtgaa                                                  19

<210> SEQ ID NO 37
<211> LENGTH: 21
<212> TYPE: DNA
<213> ORGANISM: artificial
<220> FEATURE:
<223> OTHER INFORMATION: Sense primer FimH_2_2

<400> SEQUENCE: 37
tgtgcgaaaa gccaaaacct g                                               21

<210> SEQ ID NO 38
<211> LENGTH: 19
<212> TYPE: DNA
<213> ORGANISM: artificial
<220> FEATURE:
<223> OTHER INFORMATION: antisense primer FimH_2_2

<400> SEQUENCE: 38
acgacgcggt attggtgaa                                                  19

<210> SEQ ID NO 39
<211> LENGTH: 22
<212> TYPE: DNA
<213> ORGANISM: artificial
<220> FEATURE:
<223> OTHER INFORMATION: Sense primer FimH_2_3

<400> SEQUENCE: 39
gccgcgggtt gtttataatt cg                                              22

<210> SEQ ID NO 40
<211> LENGTH: 18
<212> TYPE: DNA
<213> ORGANISM: artificial
<220> FEATURE:
<223> OTHER INFORMATION: antisense primer FimH_2_3

<400> SEQUENCE: 40
```

```
actgctcaca ggcgtcaa                                                    18

<210> SEQ ID NO 41
<211> LENGTH: 25
<212> TYPE: DNA
<213> ORGANISM: artificial
<220> FEATURE:
<223> OTHER INFORMATION: Probe FimH_2_1

<400> SEQUENCE: 41
acctctccgg cacaaccgca gatgc                                            25

<210> SEQ ID NO 42
<211> LENGTH: 25
<212> TYPE: DNA
<213> ORGANISM: artificial
<220> FEATURE:
<223> OTHER INFORMATION: Probe FimH_2_2

<400> SEQUENCE: 42
acctctccgg cacaaccgca gatgc                                            25

<210> SEQ ID NO 43
<211> LENGTH: 22
<212> TYPE: DNA
<213> ORGANISM: artificial
<220> FEATURE:
<223> OTHER INFORMATION: Probe FimH_2_3

<400> SEQUENCE: 43
cgccaccggc cacggcttat cc                                               22
```